(12) United States Patent
Beck et al.

(10) Patent No.: US 9,862,779 B2
(45) Date of Patent: Jan. 9, 2018

(54) METHOD FOR THE PRODUCTION AND SELECTION OF MOLECULES COMPRISING AT LEAST TWO DIFFERENT ENTITIES AND USES THEREOF

(71) Applicant: Hoffmann-La Roche Inc., Little Falls, NJ (US)

(72) Inventors: Mariel Beck, Penzberg (DE); Georg Tiefenthaler, Sindelsdorf (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 121 days.

(21) Appl. No.: 14/658,078

(22) Filed: Mar. 13, 2015

(65) Prior Publication Data

US 2015/0291704 A1 Oct. 15, 2015

Related U.S. Application Data

(63) Continuation of application No. PCT/EP2013/068910, filed on Sep. 12, 2013.

(30) Foreign Application Priority Data

Sep. 14, 2012 (EP) .................................... 12184473

(51) Int. Cl.
| | |
|---|---|
| C07K 16/46 | (2006.01) |
| C07K 1/107 | (2006.01) |
| C07K 16/06 | (2006.01) |
| C07K 16/28 | (2006.01) |
| C07K 16/32 | (2006.01) |
| C12N 9/52 | (2006.01) |

(52) U.S. Cl.
CPC .......... *C07K 16/468* (2013.01); *C07K 1/1075* (2013.01); *C07K 16/065* (2013.01); *C07K 16/2881* (2013.01); *C07K 16/32* (2013.01); *C12N 9/52* (2013.01); *C07K 2317/31* (2013.01); *C07K 2317/52* (2013.01); *C07K 2317/55* (2013.01); *C07K 2319/00* (2013.01); *C07K 2319/01* (2013.01); *C07K 2319/21* (2013.01); *C12Y 304/2207* (2013.01)

(58) Field of Classification Search
None
See application file for complete search history.

(56) References Cited

U.S. PATENT DOCUMENTS

| | | |
|---|---|---|
| 4,737,456 A | 4/1988 | Weng et al. |
| 5,571,894 A | 11/1996 | Wels et al. |
| 5,587,458 A | 12/1996 | King et al. |
| 5,624,821 A | 4/1997 | Winter et al. |
| 5,648,237 A | 7/1997 | Carter |
| 5,648,260 A | 7/1997 | Winter et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,153,190 A | 11/2000 | Young et al. |
| 6,171,586 B1 | 1/2001 | Lam et al. |
| 6,267,958 B1 | 7/2001 | Andya et al. |
| 6,417,429 B1 | 7/2002 | Hein et al. |
| 6,878,515 B1 | 4/2005 | Landegren |
| 7,041,440 B2 | 5/2006 | Mikoshiba et al. |
| 7,125,978 B1 | 10/2006 | Vézina et al. |
| 2002/0051986 A1 | 5/2002 | Baez et al. |
| 2005/0260186 A1 | 11/2005 | Bookbinder et al. |
| 2006/0104968 A1 | 5/2006 | Bookbinder et al. |
| 2008/0044834 A1 | 2/2008 | Heyduk |
| 2008/0280778 A1 | 11/2008 | Urdea |
| 2010/0021943 A1 | 1/2010 | An et al. |
| 2010/0062436 A1 | 3/2010 | Jarosch et al. |
| 2010/0266617 A1 | 10/2010 | Carven et al. |
| 2013/0288267 A1 | 10/2013 | Gerg et al. |
| 2013/0344094 A1 | 12/2013 | Gerg et al. |
| 2014/0249296 A1 | 9/2014 | Ploegh et al. |
| 2015/0232541 A1 | 8/2015 | Fenn et al. |
| 2015/0232560 A1 | 8/2015 | Heindl et al. |

(Continued)

FOREIGN PATENT DOCUMENTS

| | | |
|---|---|---|
| CN | 101052653 A | 10/2007 |
| JP | H08-245698 A | 9/1996 |
| JP | H09-087296 A | 3/1997 |

(Continued)

OTHER PUBLICATIONS

Levary et al., "Protein-Protein Fusion Catalyzed by Sortase A" PLoS One 6(4 Suppl e18342):1-6 ( 2011).
Marvin et al., "Recombinant approaches to IgG-like bispecific antibodies" Acta Pharmacologica Sinica 26(6):649-658 (Jun. 2005).
Strijbis, K. et al., "Protein Ligation in Living Cells Using Sortase" Traffic 13:780-789 ( 2012).
Written Opinion for PCT/EP2013/068910.
Burton. "Immunoglobulin G: Functional Sites," *Mol. Immunol.* 22(3):161-206, (1985).

(Continued)

*Primary Examiner* — Michael Burkhart
(74) *Attorney, Agent, or Firm* — Morrison & Foerster LLP

(57) ABSTRACT

Herein is reported a method for producing a polypeptide comprising at least two polypeptide domains comprising the step of cultivating a cell comprising (a) a nucleic acid encoding a soluble *S. aureus* sortase A with a C-terminal endoplasmic reticulum retention signal, (b) a nucleic acid encoding a first polypeptide domain comprising at its C-terminus a sortase motif followed by an endoplasmic reticulum retention signal, and (c) a nucleic acid encoding a second polypeptide domain comprising at its N-terminus at least a diglycine, whereby the cell secretes the sortase A conjugate of the first polypeptide domain and the second polypeptide domain, thereby producing a polypeptide comprising at least two polypeptide domains.

13 Claims, 4 Drawing Sheets

(56) References Cited

U.S. PATENT DOCUMENTS

| | | | |
|---|---|---|---|
| 2015/0232561 A1 | 8/2015 | Fenn et al. | |
| 2015/0291704 A1* | 10/2015 | Beck | C07K 16/065 530/387.3 |

FOREIGN PATENT DOCUMENTS

| | | |
|---|---|---|
| JP | 2000-135095 A | 5/2000 |
| JP | 2007-531513 A | 11/2007 |
| JP | 2008-518605 A | 6/2008 |
| JP | 2014-525904 A | 10/2014 |
| JP | 5766296 B2 | 8/2015 |
| RU | 2352583 C2 | 4/2006 |
| RU | 2433831 C2 | 11/2011 |
| WO | WO-93/16185 A2 | 8/1993 |
| WO | WO-93/16185 A3 | 8/1993 |
| WO | WO-1995/05399 A1 | 2/1995 |
| WO | WO-2005/117973 A2 | 12/2003 |
| WO | WO-2005/047334 A1 | 5/2005 |
| WO | WO-2005/047335 A1 | 5/2005 |
| WO | WO-2005/047336 A1 | 5/2005 |
| WO | WO-2005/047337 A1 | 5/2005 |
| WO | WO-2005/051976 A2 | 6/2005 |
| WO | WO-2005/074417 A2 | 8/2005 |
| WO | WO-2005/074417 A3 | 8/2005 |
| WO | WO-2006/028956 A2 | 3/2006 |
| WO | WO-2006/028956 A3 | 3/2006 |
| WO | WO-2006/044908 A2 | 4/2006 |
| WO | WO-2006/044908 A3 | 4/2006 |
| WO | WO-2006/137932 A2 | 12/2006 |
| WO | WO-2006/137932 A3 | 12/2006 |
| WO | WO-2007/108013 A2 | 9/2007 |
| WO | WO-2007/108013 A3 | 9/2007 |
| WO | WO-2009/007124 A1 | 1/2009 |
| WO | WO-2009/037659 A2 | 3/2009 |
| WO | WO-2009/037659 A3 | 3/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | 2010/087994 A2 | 8/2010 |
| WO | WO-2010/099536 A2 | 9/2010 |
| WO | WO-2010/099536 A3 | 9/2010 |
| WO | WO-2010/112193 A1 | 10/2010 |
| WO | WO-2010/115589 A1 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2012/085069 A2 | 6/2012 |
| WO | WO-2012/085069 A3 | 6/2012 |
| WO | WO-2012/085111 A1 | 6/2012 |
| WO | WO-2012/085113 A1 | 6/2012 |
| WO | 2013/003555 A1 | 1/2013 |

OTHER PUBLICATIONS

Charlton. "Expression and Isolation of recombinant Antibody Fragments in *E. coli*," Chapter 14 in *Methods in Molecular Biology*, B.K.C. Lo, ed., Humana Press, Totowan, NJ, 248:245-254, (2003).
Clancy et al. "Invited Review. Sortase Transpeptidases: Insights Into Mechanism, Substrate Specificty, and Inhibition," *Peptide Science* 94(4):385-396, (2010).
Dall'Acqua et al. "Contribution of Domain Interface Residues to the Stability of Antibody $C_H3$ Domain Homodimers," *Biochem.* 37:9266-9273, (1998, e-pub. Jun. 6, 1998).
Grengross. "Advances in the Production of Human Therapeutic Proteins in Yeasts and Filamentous Fungi," *Nat. Botech.* 22(11):1409-1414, (Nov. 2004, e-pub. Nov. 4, 2004).
Huber et al. "Crystallogrpahic Structure Studies of an IgG Molecule and Fc Fragment," *Nature* 264: 415-420, (Dec. 2, 1976).
Hudson et al. "Engineered Antibodies," *Nat. Med.* 9(1):129-134, (Jan. 2003).
Ilangovan et al. "Structure of Sortase, the Transpeptidase that Anchors Proteins to the Cell Wall of *Staphylococcus aureus*," *Proc. Natl. Acad. Sci. USA* 98(11):6056-6061, (May 22, 2001).

Li et al. "Optimization of Humanized IgGs in Glycoenineered *Pichia pastoris*," *Nat. Biotech.* 24(2):210-215, (Feb. 2006, e-pub. Jan. 22, 2006).
Mather. "Establishment and Characterization of Two Distinct Mouse Testicular Epithelial Cell Lines," *Biol. Reprod.* . . 23:243-251, (1980).
Mather et al. "Culture of Testicular Cell s in Hormone-Supplemented Serum-Free Medium," *Annals N.Y. Acad. Sci.* 383:44-68, (1982).
McCarron et al. "Antibody Conjugates and Therapeutic Strategies," *Mol. Interventions* 5(6):368-380, (Dec. 2005).
Meissner et al. "Transient Gene Experssion: Recombinant Protein Production with Suspension-Adapted HEK293-EBNA Cells," *Biotechnol. Bioeng.* 75:197-203, (2001).
Plückthun. "Antibodies from *Escherichia coli*," The Pharmacology of Monoclonal Antibodies, Rosenburg and Moore (eds.), Springer-Verlag, New York, vol. 113, pp. 269-315, (1994).
Popp et al. "Making and Breaking Peptide Bonds: Protein Engineering Using Sortase," *Angew. Chem. Int. Ed.* 50:5024-5032, (2011).
Roux et al. "Comparisons of the Ability of Human IgG3 Hinge Mutants, IgM, IgE, and IgA2, to Form Small Immune Complexes: A Role for Flexibility and Geometry," *J. Immunol.* 161(8):4083-4090, (1998).
Thies et al. "Folding and Association of the Antibody Domain $C_H3$: Prolyl Isomerization Preceeds Dimerization," *J. Mol. Biol.* 293:67-79, (1999).
Ton-That et al. "Purification and Characterization of Sortase, the Transpeptidase that Cleaves Surface Proteins of *Staphylococcus aureus* at the LPXTG Motif," *Proc. Natl. Acad. Sci. U.S.A.* 96(22):12424-12429, (Oct. 26, 1999).
Tsukiji et al. "Sortase-Mediated Ligation: A Gift from Gram-Positive Bacteria to Protein Engineering", *Chembiochem*, 10(5):787-798, (2009).
Urlaub et al. "Isolation of Chinese Hamster Cell Mutants Deficient in Dihydrofolate Reductase Activity," *Proc. Natl. Acad. Sci. USA* 77(7):4216-4220, (Jul. 1980).
Yazaki et al. "Expression of Recombinant Antibodies in Mammalian Cell Lines," Chapter 15 in *Methods in Moelcualr Biology Antibody Engineering*, B.K.Co. Lo, (ed)., Humana Press, Totowa, NJ, 248:255-268.
International Search Report dated Nov. 4, 2013, for PCT Application No. PCTEP2013/068910, filed on Sep. 12, 2013, 5 pages.
Bolscher et al. "Sortase A as a Tool for High-Yield Histatin Cyclization," *The FASEB Journal* 25(8):2650-2658, (Aug. 2011; e-published on Apr. 27, 2011).
Brorson et al., "Mutational Analysis of Avidity and Fine Specificity of Anti-Levan Antibodies," *J. Immunol.* 163:6694-6701, (1994).
Brummell et al. "Probing the Combining Site of an Anti-Carbohydrate Antibody by Saturation-Mutagenesis: Role of the Heavy-Chain CDR3 Residues," *Biochemistry* 32(4):1180-1187, (1993).
Burks et al. "In Vitro Scanning Saturation Mutagenesis of an Antibody Binding Pocket," *PNAS* 94(2):412-417, (1997).
Chames et al. "Bispecific Antibodies for Cancer Therapy", *Current Opinion in Drug Discovery & Development* 12(2):276-283, (2009).
Chan et al. "Therapeutic Antibodies for Autoimmunity and Inflammation," *Nature Reviews* 10(5):301-316, (2010).
Chen et al. "Improved Variants of SrtA for Site-Specific Conjugation on Antibodies and Proteins with High Efficiency," *Scientific Reports* 6:31899, pp. 1-12, (2016, e-published on Aug. 18, 2016).
Coleman. "Effects of Amino Acid Sequence Changes on Antibody-Antigen Interactions," *Research in Immunol.* 145(1):33-36, (1994).
Dufner et al. "Harnessing Phage and Ribosome Display for Antibody Optimization," *Trends Biotechol.* 24(11):523-529, (2006).
Goldenberg et al. "Multifunctional Antibodies by the Dock-and-Lock Method for Improved Cancer Imaging and Therapy by Pretargeting," *J. Nuc. Med.* 49(1):158-163, (Jan. 2008).
Hayashi et al. "Application of L-DNA as a Molecular Tag," *Nucl. Acids Symp. Ser.* 49:261-262, (2005).
Jang et al., "The Structural Basis for DNA Binding by an Anti-DNA Autoantibody," *Mol. Immunol.* 35(18):1207-1217 (1998).

(56) References Cited

OTHER PUBLICATIONS

Kobayashi et al. "Tryptophan H33 Plays an Important Role in Pyrimidine (6-4) Pyrimidone Photoproduct Binding by a High-Affinity Antibody," *Protein Engineering* 12(10):879-844, (1999).

Kontermann et al. "Dual Targeting Strategies with Bispecific Antibodies," *MABS Landes Bioscience* 4(2):182-197, (Mar./Apr. 2012).

Kostelny et al. "Formation of a Bispecific Antibody by the Use of Leucine Zippers," *J. Immunol.* 148:1547-1553, (Mar. 1, 1992).

Levary et al. "Protein-Protein Fusion Catalyzed by Sortase A," *PLOS One* 6:e18342.1-e18342.6, (2011). Supplementary material, eight pages.

Madej et al. "Engineering of an Anti-epidermal Growth Factor Receptor Antibody to Single Chain Format and Labeling by Sortase A-mediated Protein Ligation", *Biotechnology and Bioengineering* 109(6):1461-1470, (2012).

Möhlmann et al. "In Vitro Sortagging of an Antibody Fab Fragment: Overcoming Unproductive Reactions of Sortase with Water and Lysine Side Chains", *Chembiochem: A European Journal of Chemical Biology*, 12(11):1774-1780, (2011).

Müller et al. "A Dimeric Bispecific Miniantibody Combines Two Specificities with Avidity," *FEBS Lett.* 432:45-49, (1998).

Pack et al. "Miniantibodies: Use of Amphipathic Helices to Produce Functional, Flexibly Linked Dimeric $F_V$ Fragments with High Avidity in *Escherichia coli*," *Biochem.* 31(6):1579-1584, (Feb. 18, 1992).

Sakamoto et al. "Enzyme-Mediated Site-Specific Antibody-Protein Modification Using a ZZ Domain as a Linker," *BioConjugate Chem.* 21:2227-2233, (2010, e-pub. Nov. 11, 2010).

Strop et al. "Generating Bispecific Human IgG1 and IgG2 Antibodies from Any Antibody Pair," *Journal of Molecular Biology* 420(3):204-219, (2012).

Swee et al. "Sortase-mediated modification of αDEC205 affords optimization of antigen presentation and immunization against a set of viral epitopes," *PNAS* 110(4):1428-1433, (2013).

Ta et al. "Enzymatic Single-Chain Antibody Tagging a Universal Approach to Targeted Molecular Imaging and Cell Homing in Cardiovascular Disease," *Circulation Research* 109(4):365-373, (Aug. 5, 2011).

Wagner et al. "Bispecific Antibody Generated with Sortase and Click Chemistry has Broad Antiinfluenza Virus Activity," *Proc. Natl. Acad. Sci. USA* 111(47):16820-16825, (Nov. 25, 2014).

Witte et al. "Preparation of Unnatural N-to-N and C-to-C Protein Fusions", *Proceedings of the National Academy of Sciences of the United States of America* 109(30):11993-11998, (Jul. 24, 2012).

International Search Report dated Aug. 13, 2013, for PCT Patent Application No. PCT/EP2013/063259, filed on Jun. 25, 2013, six pages.

International Search Report dated Aug. 5, 2014, for PCT Patent Application No. PCT/EP2013/063258, filed on Jun. 25, 2013, seven pages.

International Search Report dated Aug. 6, 2013, PCT Patent Application No. PCT/EP2013/063260, filed on Jun. 25, 2013, seven pages.

Written Opinion (Second) of the International Searching Authority dated Jul. 11, 2014, for PCT Patent Application No. PCT/EP2013/063259, filed on Jun. 25, 2013, seven pages.

Written Opinion of the International Searching Authority dated Aug. 13, 2013, for PCT Patent Application No. PCT/EP2013/063259, filed on Jun. 25, 2013, six pages.

Written Opinion of the International Searching Authority dated Aug. 5, 2014, for PCT Patent Application No. PCT/EP2013/063258, filed on Jun. 25, 2013, seven pages.

Written Opinion of the International Searching Authority dated Aug. 6, 2013, PCT Patent Application No. PCT/EP2013/063260, filed on Jun. 25, 2013, eight pages.

Antos et al. "A Straight Path to Circular Proteins," *JBC* 284(23):16028-16036, (Jun. 5, 2009).

Schouten, A. et al. (1996). "The C-Terminal KDEL Sequence Increases the Expression Level of a Single-Chain Antibody Designed to be Targeted to Both the Cytosol and the Secretory Pathway in Transgenic Tobacco," *Plant Molecular Biology* 30:781-793.

\* cited by examiner

METHOD FOR THE PRODUCTION AND SELECTION OF MOLECULES COMPRISING AT LEAST TWO DIFFERENT ENTITIES AND USES THEREOF

CROSS REFERENCE TO RELATED APPLICATION

This application is a continuation of International Application No. PCT/EP2013/068910 having an international filing date of Sep. 12, 2013, the entire contents of which are incorporated herein by reference, and which claims benefit under 35 U.S.C. §119 to European Patent Application No. 12184473.2 filed Sep. 14, 2012.

SEQUENCE LISTING

The instant application contains a Sequence Listing submitted via EFS-Web and hereby incorporated by reference in its entirety. Said ASCII copy, created on Jun. 22, 2015, is named P31245-US-C_SL.txt, and 76,608 bytes in size.

Herein is reported a method for producing and selecting molecules formed by the combination of two different entities, such as binding entities, effector entities, or payloads, by using a transpeptidase, such as sortase A, wherein the at least two different entities are joined in vivo. This has been achieved by adding an endoplasmic reticulum retention signal to the sortase and to one of the entities.

BACKGROUND OF THE INVENTION

Over the past years, a wide variety of specific therapeutic proteins, including antibodies, antibody fragments, and ligands for cell surface receptors have been developed and clinically tested. Exemplary proteins are antibodies, Fc-region conjugates, or targeted delivery vehicles. Some of these therapeutic proteins have been conjugated to several classes of therapeutic toxins such as small molecule drugs, enzymes, radioisotopes, protein toxins, and other toxins for specific delivery to patients.

Effective delivery to the site of disease is a prerequisite for high efficacy and low toxicity of any therapeutic molecule. For example, antibodies can participate in this context. If the antibody is not the therapeutic principle by itself, conjugation of an effector molecule to an antibody makes it possible to achieve precise localization of the drug at the desired site within the human body. This increases the effective drug concentration within this target area, thereby optimizing the therapeutic efficacy of the agent. Furthermore, with targeted delivery, the clinician may be able to lower the overall dose of the therapeutic agent and, thus, minimize systemic exposure—something that is particularly relevant if the drug payload has associated toxicities or if it is to be used in the treatment of chronic conditions (see e.g. McCarron, P. A., et al., Mol. Interventions 5 (2005) 368-380).

In WO 2010087994 methods for ligation and uses thereof are reported. Recombinant approaches to IgG-like bispecific antibodies are reported by Marvin, J. S., et al. (Acta Pharmacol. Sinica 26 (2005) 649-658). Levary, D. A., et al. (PLoS one, 6 (2011) e18342.1-e18342.6) report protein-protein fusion catalyzed by sortase A. In WO 2013/003555 the use of sortases to install click chemistry handles for protein ligation is reported.

Strijbis, K. et al (Traffic 13 (2012) 780-789) report protein ligation in living cells using sortase. It has been stated by them that the $Ca^{2+}$-dependent *S. aureus* sortase A is not functional intracellularly, but that the $Ca^{2+}$-independent *S. pyogenes* sortase A is functional in the cytosol and endoplasmic reticulum (ER) lumen of both *Saccharomyces cerevisiae* and mammalian HEK293T cells.

SUMMARY OF THE INVENTION

Herein is reported a method for producing in vivo intracellularly an enzyme—catalyzed (i.e. enzymatic) conjugate of a first polypeptide domain with a second polypeptide domain by using the $Ca^{2+}$-dependent enzyme sortase A of *Staphylococcus aureus* (*S. aureus*), whereby one of the polypeptide domains and the soluble sortase A enzyme contain an endoplasmic reticulum retention signal sequence.

This technology is especially suited for the rapid generation e.g. of a library of combinations of a first group of polypeptide domains (e.g. a first group of binding domains such as cognate pairs of antibody variable domains) and a second group of polypeptide domains (e.g. a second group of binding domains such as cognate pairs of antibody variable domains but directed against other epitopes/antigens as those of the first group, or a group of payload molecules). This library can be easily generated e.g. by transient transfection in HEK cells and the resulting combinations can be screened thereafter e.g. for the intended biological effect or intended properties.

One aspect as reported herein is a method for producing a polypeptide comprising at least two polypeptide domains comprising the step of cultivating a cell comprising
  a) a nucleic acid encoding a soluble sortase A with a C-terminal endoplasmic reticulum retention signal,
  b) a nucleic acid encoding a first polypeptide domain comprising at its C-terminus or in its C-terminal region a sortase motif followed by an endoplasmic reticulum retention signal, and
  c) a nucleic acid encoding a second polypeptide domain comprising at its N-terminus an oligoglycine motif of at least two glycine residues,
whereby the cell secretes the sortase A(-mediated/-catalyzed) conjugate of the first polypeptide domain and the second polypeptide domain,
thereby producing a polypeptide comprising at least two polypeptide domains.

One aspect as reported herein is a method for producing a multispecific binder comprising at least two binding entities comprising the step of cultivating a cell comprising
  a) a nucleic acid encoding a soluble sortase A with a C-terminal endoplasmic reticulum retention signal,
  b) a nucleic acid encoding a first binding entity comprising at its C-terminus or in its C-terminal region a sortase motif followed by an endoplasmic reticulum retention signal, and
  c) a nucleic acid encoding a second binding entity comprising at its N-terminus at least a diglycine,
whereby the cell secretes the sortase A(-mediated/-catalyzed) conjugate of the first binding entity and the second binding entity,
whereby the first binding entity specifically binds to a first antigen or target and the second binding entity specifically binds to a second antigen or target,
thereby producing a multispecific binder comprising at least two binding entities.

In one embodiment of all aspects is the sortase A the sortase A of *Staphylococcus aureus* (*S. aureus*). In one embodiment the nucleic acid encoding a (soluble) sortase A with a C-terminal endoplasmic reticulum retention signal encodes an amino acid sequence of SEQ ID NO: 51 or SEQ ID NO: 52.

Herein is reported a method for providing tailor-made, highly specific therapeutic molecules for the treatment of a disease, such as cancer or a viral infection, in a patient in need of a treatment, whereby the therapeutic molecule is adapted to the characteristics of the disease of the patient and/or to the genotype/phenotype of the patient.

Such adaptation is achieved by making a tailor-made molecule taking into account the genotype/phenotype of the disease harboring/affected cells of the patient.

In a first step the genotype/phenotype of the cells (e.g. the presence and number/quantity of disease-specific cell surface molecules) that are intended to be targeted with the therapeutic molecule is determined. This can be achieved, e.g. by cell imaging techniques such as immunohistochemical staining (IHC, immunohistochemistry) of patient's cells derived e.g. from blood and/or biopsied material using fluorescently labeled monospecific (therapeutic or diagnostic) antibodies. Alternatively the genotype/phenotype of the cells can be analyzed after staining with labeled therapeutic or diagnostic antibodies using FACS-based methods. In vivo imaging techniques including optical imaging, molecular imaging, fluorescence imaging, bioluminescence Imaging, MRI, PET, SPECT, CT, and intravital microscopy may be used also for determination of the genotype/phenotype of disease-related cells of a patient. Depending on the determined genotype/phenotype of the disease-related cells of a patient a tailor-made combination of targeting/binding entities can be/is chosen and are combined in a therapeutic molecule. Such a therapeutic molecule may be for example a bispecific antibody.

Such tailor-made therapeutic molecules i) will be highly specific, ii) will have a good therapeutic efficacy, and iii) will induce fewer and/or less severe side effects compared to conventionally chosen therapeutics. This can be achieved by endowing the therapeutic molecule with improved targeting and/or improved tailor-made delivery properties, e.g. for delivery of a therapeutic payload to its intended site of action.

The improved delivery of the therapeutic molecule to its site of action, such as e.g. a cancer cell, can be achieved by a higher/increased selectivity and/or specificity for the targeted therapeutic molecule compared to conventionally chosen therapeutic molecules. The therapeutic molecule comprises at least two entities that specifically bind to or can be bound by different proteins (e.g. two different cell surface markers).

The increased selectivity and/or specificity of the tailor-made therapeutic molecule can be achieved by the simultaneous binding of both targeting entities to their respective targets/epitopes or by the simultaneous binding of both polypeptide domains by its interaction partner, or by mixtures thereof.

Especially suited is the combination of two binding entities having a low to medium affinity for their respective targets/epitopes. Additionally, off-target binding is greatly reduced or can even be eliminated totally.

It has been found that with the method as reported herein it is possible to tailor-make e.g. bispecific binders such as e.g. bispecific antibodies specifically directed to two surface markers found on the surface of a cell, such as a cancer cell. As the binding specificities are individually provided by the starting components it is possible to tailor-make a multispecific targeting and binding molecule simply by determining the surface markers present on a cell, e.g. on a cancer cell, and conjugating the respective antibody fragments that specifically bind to these surface markers or their respective ligands by an enzymatic procedure. As the enzymatic conjugation is performed by the enzyme sortase A, in one embodiment by the sortase A of S. aureus, the resulting bispecific binder (bispecific antibody) is characterized by the presence of the amino acid sequence LPXTG (SEQ ID NO: 01, wherein X can be any amino acid residue).

One aspect as reported herein is a method for selecting a multispecific binder that specifically binds to two different epitopes or antigens comprising the step of
  selecting from a multitude of multispecific binders comprising different combinations of a first binding entity and a second binding entity a multispecific binder that specifically binds to two different epitopes or antigens.

One aspect as reported herein is a method for selecting a bispecific antibody comprising the following steps
  (i) determining the cell surface makers present in a cell containing sample and selecting thereof at least a first surface marker and a second surface marker,
  (ii) transfecting a cell with (a) a nucleic acid encoding an antibody Fab, or scFab fragment, or an scFv antibody comprising within the 20 (twenty) C-terminal amino acid residues the amino acid sequence LPXTG (SEQ ID NO: 01, wherein X can be any amino acid residue) followed by an endoplasmic reticulum retention signal KDEL (SEQ ID NO: 02), whereby the Fab, or scFab fragment, or scFv antibody specifically binds to the first surface marker or its ligand, (b) a nucleic acid encoding a one-armed antibody fragment comprising a full length antibody heavy chain, a full length antibody light chain, and an antibody heavy chain Fc-region polypeptide, whereby the full length antibody heavy chain and the full length antibody light chain are cognate antibody chains complementary to each other and the pair of variable domains (VH and VL) thereof forms an antigen binding site that specifically binds to the second surface marker or its ligand, whereby the full length antibody heavy chain and the antibody heavy chain Fc-region polypeptide are covalently linked to each other via one or more disulfide bonds forming an antibody hinge region, and whereby the antibody heavy chain Fc-region polypeptide has an oligoglycine $G_m$ (m=2, or 3, or 4, or 5) (SEQ ID NO: 53) amino acid sequence at its N-terminus, and (c) a nucleic acid encoding a soluble sortase A with a C-terminal endoplasmic reticulum retention signal,
  and thereby producing the bispecific antibody.

One aspect as reported herein is a method for determining a combination of antigen binding sites comprising the following steps:
  (i) determining the binding specificity and/or selectivity and/or affinity and/or effector function and/or in vivo half-life of a multitude of bispecific antibodies prepared by combining (a) each member of a first multitude of antibody Fab, or scFab fragments, or scFv antibody fragments whereby each member comprises within the 20 C-terminal amino acid residues the amino acid sequence LPXTG (SEQ ID NO: 01, wherein X can be any amino acid residue) followed by an endoplasmic reticulum retention signal KDEL (SEQ ID NO: 02), whereby the Fab, or scFab fragment, or scFv antibody specifically binds to a first epitope or antigen, with (b) each member of a multitude of one-armed antibody fragments comprising a full length antibody heavy chain, a full length antibody light chain, and an antibody heavy chain Fc-region polypeptide, whereby the full length antibody heavy chain and the full length antibody light chain are cognate antibody chains complementary to each other and the pair of variable domains (VH and VL) thereof forms an antigen binding site that specifically binds to a second epitope or antigen, whereby the full length antibody heavy chain and the antibody heavy chain Fc-region polypeptide are covalently linked to each other via one or more disulfide bonds forming an antibody hinge region, and whereby the antibody heavy chain Fc-region polypeptide has an oligoglycine $G_m$ (m=2, or 3, or 4, or 5) (SEQ ID NO: 53) amino acid sequence at its N-terminus, covalently by a sortase A catalyzed enzymatic reaction, and (ii) choosing the bispecific antibody with suitable binding specificity and/or selectivity and/or affinity and/or effector function and/or in vivo half-life and thereby determining a combination of antigen binding sites.

In one embodiment of all aspects is the sortase A the sortase A of Staphylococcus aureus (S. aureus). In one embodiment the nucleic acid encoding a (soluble) sortase A with a C-terminal endoplasmic reticulum retention signal encodes an amino acid sequence of SEQ ID NO: 51 or SEQ ID NO: 52.

One aspect as reported herein is a bispecific antibody obtained by a method as reported herein.

One aspect as reported herein is a bispecific antibody comprising the amino acid sequence LPXTG (SEQ ID NO: 01, wherein X can be any amino acid residue) in one of its heavy chains.

In the following embodiments of all aspects as reported herein are given.

In one embodiment the members of the multitude of multispecific binders are each obtained by a method as reported herein.

In one embodiment a multispecific binder is selected based on its binding specificity and/or selectivity and/or affinity and/or effector function and/or in vivo half-life.

In one embodiment the binding entity is a cognate pair of an antibody heavy chain variable domain and an antibody light chain variable domain.

In one embodiment the multispecific binder is a bispecific antibody comprising two or four binding entities.

In one embodiment the first polypeptide domain and the second polypeptide domain are selected independently of each other from full length antibody, scFv, scFab, antibody heavy chain, antibody light chain, antibody heavy chain Fc-region fragment, pair of antibody light chain variable domain and antibody heavy chain variable domain, antigen binding antibody fragments, VH, VL, CH1, CH2, CH3, CH4, CL, antibody hinge region, cytokine, receptor, receptor ligand, detectable label, tag, and partner of a binding pair.

In one embodiment the endoplasmic reticulum retention signal is selected from SEQ ID NO: 02 (KDEL), SEQ ID NO: 03 (HDEL), or SEQ ID NO: 04 (SFIXXXXMP).

In one embodiment the sortase motif is LPXTG (SEQ ID NO: 01, wherein X can be any amino acid residue).

In one embodiment the first binding domain or the first binding entity has within the 20 C-terminal amino acid residues the amino acid sequence LPXTG (SEQ ID NO: 01, wherein X can be any amino acid residue).

In one embodiment the cell is a mammalian cell or a yeast cell. In one embodiment the mammalian cell is selected from a HEK cell, a CHO cell, or a BHK cell.

In one embodiment the Fc-region comprises a mutation of the naturally occurring amino acid residue at position 329 and at least one further mutation of at least one amino acid residue selected from the group comprising amino acid residues at position 228, 233, 234, 235, 236, 237, 297, 318, 320, 322 and 331 to a different residue, wherein the residues in the Fc-region are numbered according to the EU index of Kabat. The change of these specific amino acid residues results in an altering of the effector function of the Fc-region compared to the non-modified (wild-type) Fc-region.

In one embodiment the binding entity is selected from (or the first binding entity and the second binding entity are selected independently of each other from) the group of a darpin domain based binding entity, an anticalin domain based binding entity, a T-cell receptor fragment like scTCR domain based binding entity, a camel VH domain based binding entity, a tenth fibronectin 3 domain based binding entity, a tenascin domain based binding entity, a cadherin domain based binding entity, an ICAM domain based binding entity, a titin domain based binding entity, a GCSF-R domain based binding entity, a cytokine receptor domain based binding entity, a glycosidase inhibitor domain based binding entity, a superoxide dismutase domain based binding entity, or antibody fragments like Fab, or scFab, or scFv fragment.

In one embodiment the first polypeptide domain comprises i) the amino acid sequence LPXTG (SEQ ID NO: 01, wherein X can be any amino acid residue) in its C-terminal amino acid sequence region (i.e. within the twenty C-terminal amino acid residues) and ii) the endoplasmic reticulum retention signal KDEL (SEQ ID NO: 02) at its C-terminus, and the second polypeptide domain comprises an oligoglycine $G_m$ (m=2, or 3, or 4, or 5) (SEQ ID NO: 53) at its N-terminus.

In one embodiment the second polypeptide domain or the second binding entity comprises an oligoglycine $G_m$ (m=2, or 3, or 4, or 5) (SEQ ID NO: 53) amino acid sequence at its N-terminus.

One aspect as reported herein is a pharmaceutical formulation comprising a multispecific binder as reported herein.

One aspect as reported herein is the use of a multispecific binder as reported herein in the manufacture of a medicament.

In one embodiment the medicament is for the treatment of cancer.

One aspect as reported herein is a method of treating an individual having cancer comprising administering to the individual an effective amount of a multispecific binder as reported herein.

One aspect as reported herein is a method for destroying cancer cells in an individual comprising administering to the individual an effective amount of a multispecific binder as reported herein.

One aspect as reported herein is a pharmaceutical formulation comprising a bispecific antibody as reported herein.

One aspect as reported herein is the use of a bispecific antibody as reported herein in the manufacture of a medicament.

In one embodiment the medicament is for the treatment of cancer.

One aspect as reported herein is a method of treating an individual having cancer comprising administering to the individual an effective amount of a bispecific antibody as reported herein.

One aspect as reported herein is a method for destroying cancer cells in an individual comprising administering to the individual an effective amount of a bispecific antibody as reported herein. In one embodiment of all aspects as reported herein the Fc-region is a human Fc-region or a variant thereof.

In one embodiment the human antibody Fc-region is of human IgG1 subclass, or of human IgG2 subclass, or of human IgG3 subclass, or of human IgG4 subclass.

In one embodiment the antibody Fc-region is a human antibody Fc-region of the human IgG1 subclass, or of the human IgG4 subclass.

In one embodiment the human antibody Fc-region comprises a mutation of the naturally occurring amino acid residue at least at one of the following amino acid positions 228, 233, 234, 235, 236, 237, 297, 318, 320, 322, 329, and/or 331 to a different residue, wherein the residues in the antibody Fc-region are numbered according to the EU index of Kabat.

In one embodiment the human antibody Fc-region comprises a mutation of the naturally occurring amino acid residue at position 329 and at least one further mutation of at least one amino acid residue selected from the group comprising amino acid residues at position 228, 233, 234, 235, 236, 237, 297, 318, 320, 322 and 331 to a different residue, wherein the residues in the Fc-region are numbered according to the EU index of Kabat. The change of these specific amino acid residues results in an altering of the effector function of the Fc-region compared to the non-modified (wild-type) Fc-region.

In one embodiment the human antibody Fc-region has a reduced affinity to the human FcγRIIIA, and/or FcγRIIA, and/or FcγRI compared to a conjugate comprising the corresponding wild-type IgG Fc-region.

In one embodiment the amino acid residue at position 329 in the human antibody Fc-region is substituted with glycine, or arginine, or an amino acid residue large enough to destroy the proline sandwich within the Fc-region.

In one embodiment the mutation in the human antibody Fc-region of the naturally occurring amino acid residue is at least one of S228P, E233P, L234A, L235A, L235E, N297A, N297D, P329G, and/or P331 S.

In one embodiment the mutation is L234A and L235A if the antibody Fc-region is of human IgG1 subclass, or S228P and L235E if the antibody Fc-region is of human IgG4 subclass.

In one embodiment the antibody Fc-region comprises the mutation P329G.

In one embodiment the antibody Fc-region comprises the mutation T366W in the first heavy chain Fc-region polypeptide and the mutations T366S, L368A and Y407V in the second heavy chain Fc-region polypeptide, wherein the numbering is according to the EU index of Kabat.

In one embodiment the antibody Fc-region comprises the mutation S354C in the first heavy chain Fc-region polypeptide and the mutation Y349C in the second heavy chain Fc-region polypeptide.

DETAILED DESCRIPTION OF EMBODIMENTS OF THE INVENTION

I. Definitions

Figure 1:
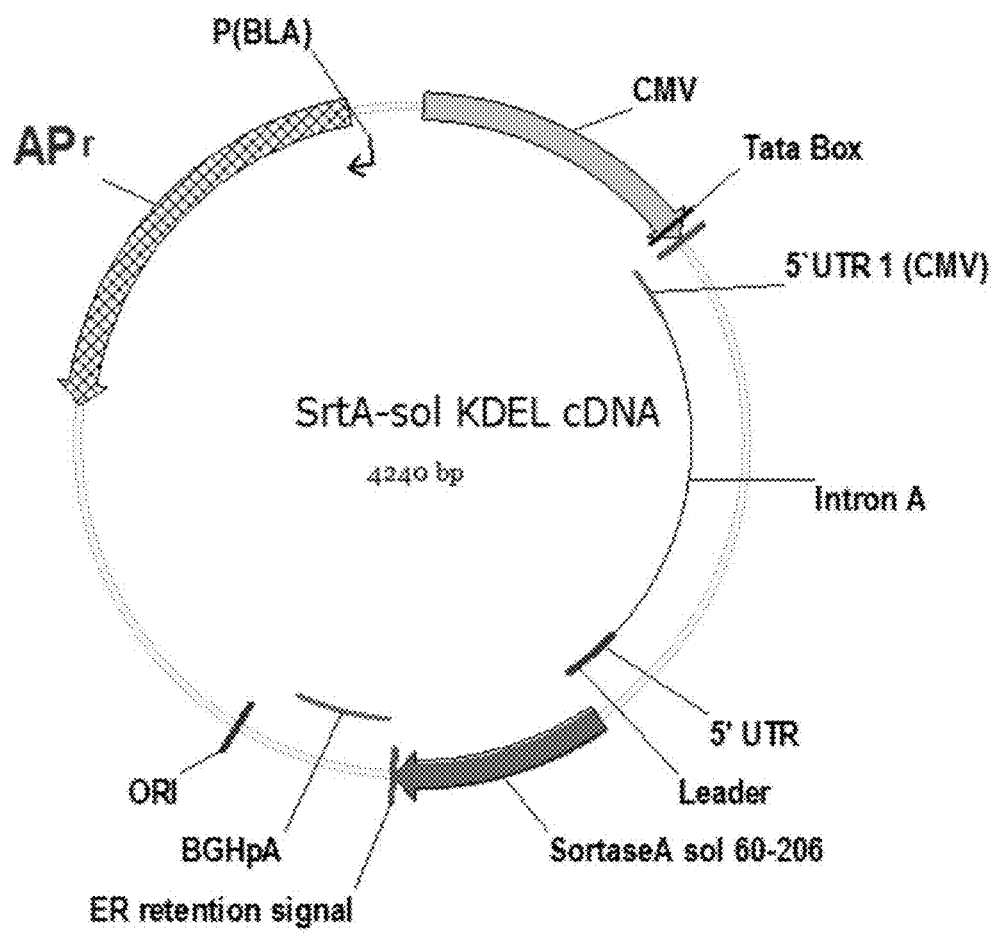
FIG. 1 Plasmid map of the expression plasmid for the soluble sortase A comprising an endoplasmic retention signal at its C-terminus.
Figure 2:
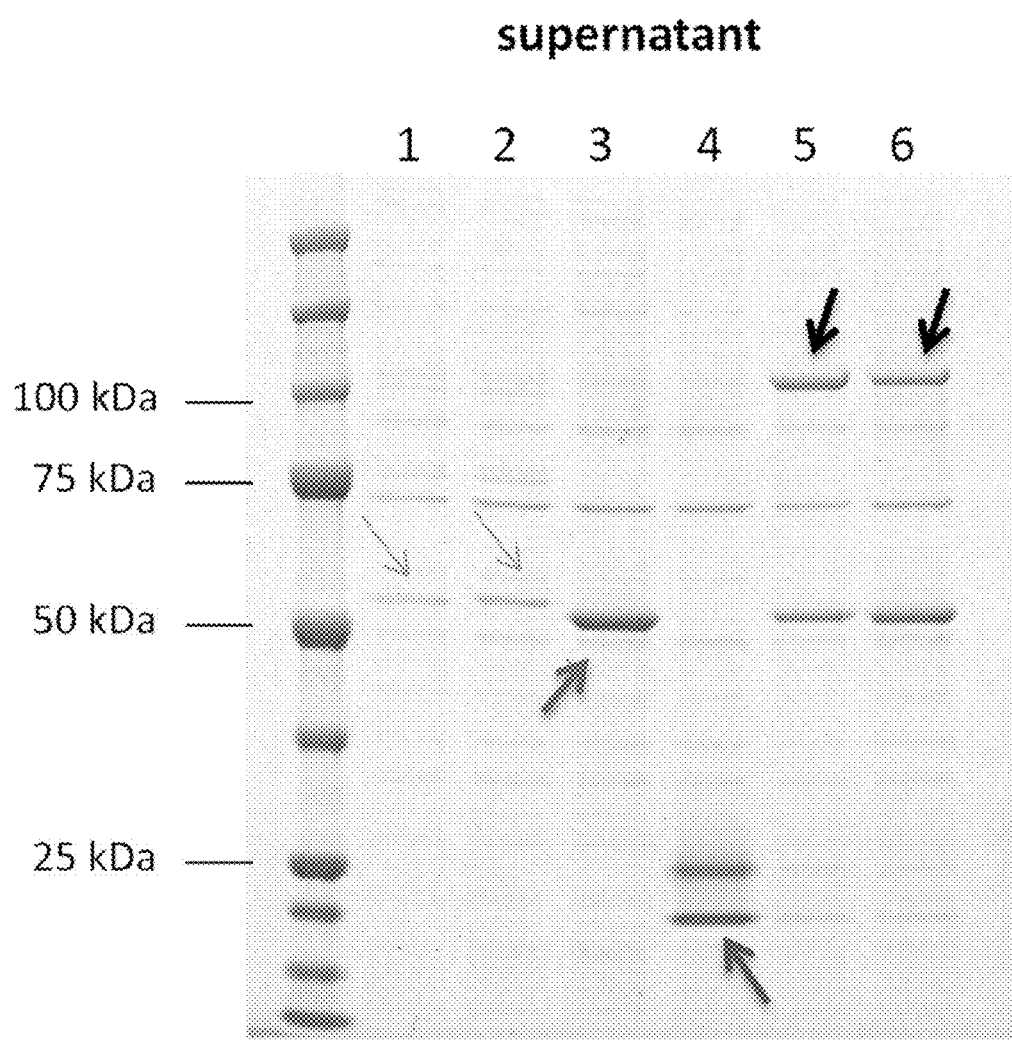
FIG. 2 Coomassie stained SDS-gel, reducing conditions; culture supernatants of HEK293 cells transfected with scFab-GS-His6-GS-LPETGGS-KDEL("GS-His6-GS-LPETGGS-KDEL" disclosed as SEQ ID NO: 29) (lane 1), scFab-GS-His6-GAPPPS-LPETGGS-KDEL ("GS-His6-GAPPPS-LPETGGS-KDEL" disclosed as SEQ ID NO: 54) (lane 2), (GGGGS)$_2$-scFab ("(GGGGS)$_2$" disclosed as SEQ ID NO: 31) (lane 3), soluble sortase A-KDEL (lane 4), combination 1+3+4 (plasmid ratios 2.5:5:1) (lane 5), combination 2+3+4 (plasmid ratio 2:8:1) (lane 6); scFab-GS-His6-GS -LPETGGS-KDEL ("GS-His6-GS-LPETGGS-KDEL" disclosed as SEQ ID NO: 29) and scFab-GS-His6-GAPPPS -LPETGGS-KDEL ("GS-His6-GAPPPS-LPETGGS-KDEL" disclosed as SEQ ID NO: 54) are retained mostly intracellularly, (GGGGS)$_2$-scFab ("(GGGGS)$_2$" disclosed as SEQ ID NO: 31) is expressed and secreted into the medium (about 50 kDa), for the combination a band at about 100 kDa of the enzymatic conjugate can be seen.
Figure 3:
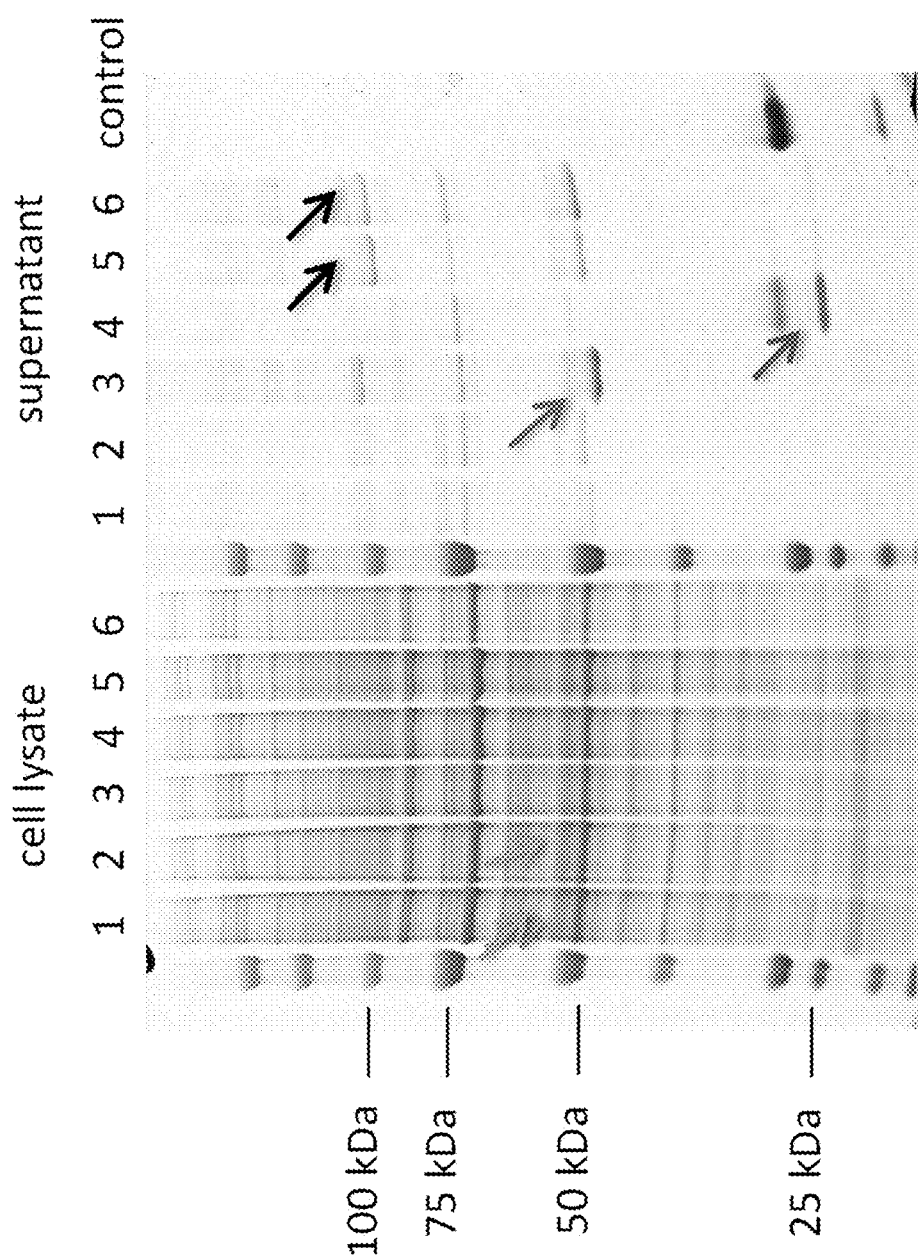
FIG. 3 Coomassie stained SDS-gel, reducing conditions; cell lysates (left) of HEK293 cells transfected with scFab-GS-His6-GS -LPETGGS-KDEL ("GS-His6-GS-LPETGGS-KDEL" disclosed as SEQ ID NO: 29) (lane 1), scFab-GS-His6-GAPPPS-LPETGGS -KDEL("GS-His6-GAPPPS-LPETGGS-KDEL" disclosed as SEQ ID NO: 54) (lane 2), (GGGGS)$_2$-scFab ("(GGGGS)$_2$" disclosed as SEQ ID NO: 31) (lane 3), soluble sortase A-KDEL (lane 4), combination 1+3+4 (plasmid ratio 2.5:5:1) (lane 5), combination 2+3+4 (plasmid ratio 2:8:1) (lane 6); scFab-GS -His6-GS-LPETGGS-KDEL ("GS-His6-GS-LPETGGS-KDEL" disclosed as SEQ ID NO: 29) and scFab-GS-His6-GAPPPS -LPETGGS-KDEL ("GS-His6-GAPPPS-LPETGGS-KDEL" disclosed as SEQ ID NO: 54) are retained mostly intracellularly.
Figure 4:
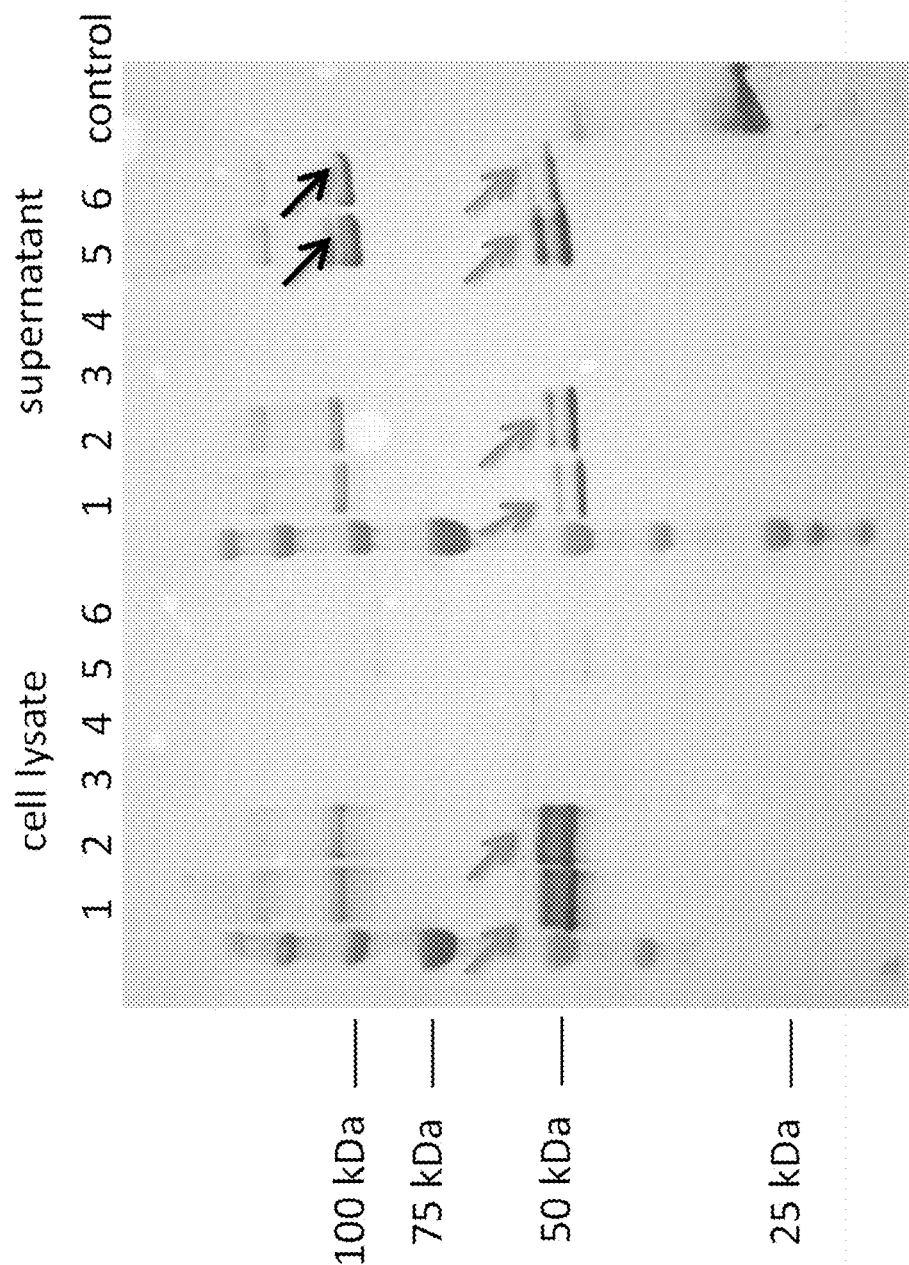
FIG. 4 Western blot analysis of an SDS gel using the identical samples and performed under identical conditions as the gels from FIGS. 2 and 3; the scFab-LPXTG ("LPXTG" disclosed as SEQ ID NO: 1) molecules and the conjugation product are detected with an anti-His-tag antibody (PentaHis-AK (Qiagen) ("PentaHis" disclosed as SEQ ID NO: 64)); for the combination a band at about 100 kDa of the enzymatic conjugate can be seen.

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "alteration" denotes the mutation, addition, or deletion of one or more amino acid residues in a parent amino acid sequence.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3xFlag-tag, Strep-tag, Nano-tag, SBP-tag, c-myc-tag, S-tag, calmodulin-binding-peptide, cellulose-binding-domain, chitin-binding-domain, GST-tag, or MBP-tag. In one embodiment the tag is selected from SEQ ID NO: 05 (RRRRR), or SEQ ID NO: 06 (RRRRRR), or SEQ ID NO: 07 (HHHHHH), or SEQ ID NO: 08 (KDHLIHNVHKEFHAHAHNK), or SEQ ID NO: 09 (DYKDDDDK), or SEQ ID NO: 10 (DYKDH-DGDYKDHDIDYKDDDDK), or SEQ ID NO: 11 (AWRH-PQFGG), or SEQ ID NO: 12 (WSHPQFEK), or SEQ ID NO: 13 (MDVEAWLGAR), or SEQ ID NO: 14 (MD-VEAWLGARVPLVET), or SEQ ID NO: 15 (MDEKTTG-WRGGHVVEGLAGELEQLRARLEHHPQGQREP), or SEQ ID NO: 16 (EQKLISEEDL), or SEQ ID NO: 17 (KETAAAKFERQHMDS), or SEQ ID NO: 18 (KRRWK-KNFIAVSAANRFKKISSSGAL), or SEQ ID NO: 19 (cellulose binding domain), or SEQ ID NO: 20 (cellulose binding domain), or SEQ ID NO: 21 (TNPGVSAWQVN-TAYTAGQLVTYNGKTYKCLQPHTSLAGWEP SNV-PALWQLQ), or SEQ ID NO: 22 (GST-tag), or SEQ ID NO: 23 (MBP-tag).

The term "antigen binding antibody fragment" denotes a molecule other than a full length antibody that comprises a portion of a full length antibody that binds the antigen to which the intact antibody binds. Examples of antibody fragments include but are not limited to Fv, scFv, Fab, scFab, Fab', Fab'-SH, F(ab')$_2$, diabodies, linear antibodies, single-chain antibody molecules (e.g. scFv), and multispecific antibodies formed from antibody fragments.

Antibody fragments include, but are not limited to, Fab, Fab', Fab'-SH, F(ab')$_2$, Fv, and scFv fragments, and other fragments described below. For a review of certain antibody fragments, see Hudson, P. J., et al., Nat. Med. 9 (2003) 129-134. For a review of scFv fragments, see, e.g., Plueckthun, A., In: The Pharmacology of Monoclonal Antibodies, vol. 113, Rosenburg and Moore (eds.), Springer-Verlag, New York (1994), pp. 269-315; see also WO 93/16185; U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Antibody fragments can be made by various techniques, including but not limited to proteolytic digestion or cleavage of an intact antibody as well as production by recombinant host cells (e.g. *E. coli* or phage or eukaryotic cells), as described herein.

The term "bispecific antibody" denotes an antigen binding molecule that can specifically bind to a first antigen or epitope and to a second antigen or epitope, whereby the first antigen or epitope is different from the second antigen or epitope.

Bispecific antibody formats are described e.g. in WO 2009/080251, WO 2009/080252, WO 2009/080253, WO 2009/080254, WO 2010/112193, WO 2010/115589, WO 2010/136172, WO 2010/145792, and WO 2010/145793.

The term "class" of an antibody denotes the type of constant domain or constant region possessed by its heavy chain. There are five major classes of antibodies in humans: IgA, IgD, IgE, IgG, and IgM, and several of these may be further divided into subclasses (isotypes), e.g., IgG1, IgG2, IgG3, IgG4, IgA1, and IgA2. The gene segments encoding the heavy chain constant domains that correspond to the different classes of immunoglobulins are called α, δ, ε, γ, and μ, respectively. In addition, there are two classes of light chains present in antibodies of human origin: kappa and lambda which can form intact antibodies in combination with their cognate heavy chain partners. The genes encoding the kappa or lambda light chains are called κ and λ, respectively.

The term "effector function" denotes those biological activities attributable to the Fc-region of an antibody, which vary with the antibody class and/or subclass. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP); down regulation of cell surface receptors (e.g. B-cell receptor); and B-cell activation. Such function can be effected by, for example, binding of an Fc-region to an Fc receptor on an immune cell with phagocytic or lytic activity, or by binding of an Fc-region to components of the complement system.

An "effective amount" of an agent, e.g., a pharmaceutical formulation, refers to an amount effective, at dosages and for periods of time necessary, to achieve the desired therapeutic or prophylactic result.

The term "Fc-region" denotes the C-terminal region of an immunoglobulin. The Fc-region is a dimeric molecule comprising two disulfide-linked antibody heavy chain fragments (heavy chain Fc-region polypeptide chains). An Fc-region can be generated by papain digestion, or IdeS digestion, or trypsin digestion of an intact (full length) antibody or can be produced recombinantly.

The Fc-region obtainable from a full length antibody or immunoglobulin comprises at least residues 226 (Cys) to the C-terminus of the full length heavy chain and, thus, comprises a part of the hinge region and two or three constant region domains, i.e. a CH2 domain, a CH3 domain, and an additional/extra CH4 domain in case of IgE and IgM class antibodies. It is known from U.S. Pat. Nos. 5,648,260 and 5,624,821 that the modification of defined amino acid residues in the Fc-region results in phenotypic effects.

The formation of the dimeric Fc-region comprising two identical or non-identical antibody heavy chain fragments is mediated by the non-covalent dimerization of the comprised CH3 domains (for involved amino acid residues see e.g. Dall'Acqua, Biochem. 37 (1998) 9266-9273). The Fc-region is covalently stabilized by the formation of disulfide bonds in the hinge region (see e.g. Huber, et al., Nature 264 (1976) 415-420; Thies, et al., J. Mol. Biol. 293 (1999) 67-79). The introduction of amino acid residue changes within the CH3 domain in order to disrupt the dimerization of CH3-CH3 domain interactions do not adversely affect the neonatal Fc receptor (FcRn) binding due to the location of the residues involved in CH3-CH3-domain dimerization which are located on the inner interface of the CH3 domains, whereas the residues involved in Fc-region-FcRn interaction are located on the outside of the CH2-CH3 domains.

The residues associated with effector functions of an Fc-region are located in the hinge region, the CH2, and/or the CH3 domains as determined for a full length antibody molecule. The Fc-region associated/mediated functions are:
  (i) antibody-dependent cellular cytotoxicity (ADCC),
  (ii) complement (C1q) binding, activation and complement-dependent cytotoxicity (CDC),
  (iii) antibody-dependent cellular phagocytosis (ADCP)
  (iv) phagocytosis/clearance of antigen-antibody complexes (immune complexes),
  (v) cytokine release in some instances, and
  (vi) half-life/clearance rate of antibody and antigen-antibody complexes.

The Fc-region-associated effector functions are triggered/initiated by the interaction of the Fc-region with effector function specific molecules or receptors. Predominantly antibodies of the IgG1 subclass can effect receptor activation, whereas antibodies of the IgG2 and IgG4 subclasses do not have effector function or have limited effector function.

The effector function eliciting receptors are the Fc receptor types (and sub-types) FcγRI, FcγRII and FcγRIII. The effector functions associated with an IgG1 subclass can be reduced by introducing specific amino acid changes in the lower hinge region, such as L234A and/or L235A, which are involved in FcγR and C1q binding. Also certain amino acid residues, especially located in the CH2 and/or CH3 domains, are associated with the control of the circulation half-life of an antibody molecule or an Fc-region fusion polypeptide in the blood stream. The circulation half-life is determined by the binding of the Fc-region to the neonatal Fc receptor (FcRn).

The term "human Fc-region" denotes the C-terminal region of an immunoglobulin heavy chain of human origin that contains at least a part of the hinge region, the CH2 domain and the CH3 domain. In one embodiment, a human IgG antibody heavy chain Fc-region extends from about Glu216, or from about Cys226, or from about Pro230, to the carboxyl-terminus of the heavy chain. However, the C-terminal lysine (Lys447) of the antibody Fc-region may or may not be present.

A polypeptide chain of a wild-type human Fc-region of the IgG1 subclass has the following amino acid sequence:

(SEQ ID NO: 24)
CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK.

A polypeptide chain of a wild-type human Fc-region of the IgG4 subclass has the following amino acid sequence:

(SEQ ID NO: 25)
CPSCPAPEFLGGPSVFLFPPKPKDTLMISRTPEVTCVVVDVSQEDPEVQF

NWYVDGVEVHNAKTKPREEQFNSTYRVVSVLTVLHQDWLNGKEYKCKVSN

KGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSC

SVMHEALHNHYTQKSLSLSLGK.

The term "full length antibody" denotes an antibody having a structure and amino acid sequence substantially identical to a native antibody structure as well as polypeptides that comprise the Fc-region as reported herein.

The term "full length antibody heavy chain" denotes a polypeptide comprising in N- to C-terminal direction an antibody variable domain, a first constant domain, an antibody heavy chain hinge region, a second constant domain, and a third constant domain, and in some instances a fourth constant domain.

The term "antibody heavy chain Fc-region" denotes a polypeptide comprising an antibody heavy chain hinge region, a first constant domain (normally the CH2 domain), and a second constant domain (normally the CH3 domain).

The term "CH2 domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 26 (APELLGGPSVFLFPPKPKDTLMISRTPEVTCVWDVSHEDPEVKFNWYVDG VEVHNAKTKPREEQESTYRWSVLTVLHQDWLNGKEYKCKVSNKALPAPI EKTISKAK). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain has the amino acid sequence of SEQ ID NO: 27 (GQPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQKS LSLSPG).

The term "full length antibody light chain" denotes a polypeptide comprising in N- to C-terminal direction an antibody variable domain and a constant domain.

The term "hinge region" denotes the part of an antibody heavy chain polypeptide that joins in a wild-type antibody heavy chain the CH1 domain and the CH2 domains, e.g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimer consisting of two polypeptides with identical amino acid sequence. The hinge region generally comprises about 25 amino acid residues and is flexible allowing the antigen binding regions to move independently of each other. The hinge region can be subdivided into three subdomains: the upper, the middle, and the lower hinge region (see e.g. Roux, et al., J. Immunol. 161 (1998) 4083).

The term "lower hinge region" of an Fc-region denotes the stretch of amino acid residues immediately C-terminal to the middle (central) hinge region, i.e. residues 233 to 239 of the Fc-region according to the EU numbering of Kabat.

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

The term "individual" or "subject" denotes a mammal. Mammals include, but are not limited to, domesticated animals (e.g. cows, sheep, cats, dogs, and horses), primates (e.g., humans and non-human primates such as monkeys), rabbits, and rodents (e.g., mice, rats, and hamsters). In certain embodiments, the individual or subject is a human.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Sequence alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such a form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "phenotype of a patient" denotes the composition of cell surface molecules/receptors in a kind of cells from a patient. The composition can be a qualitative as well as a quantitative composition. The cells for which the genotype is determined/given can be a single cell or a sample comprising cells.

The term "position" denotes the location of an amino acid residue in the amino acid sequence of a polypeptide. Positions may be numbered sequentially, or according to an established format, for example the EU index of Kabat for antibody numbering.

The term "receptor" denotes a polypeptide capable of binding at least one ligand. In one embodiment the receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

II. Tailor-Made Molecules Comprising a First and a Second Polypeptide Domain

It has been found that by using a modular approach as reported herein tailor-made therapeutic polypeptides can be provided. These polypeptides are tailor-made with respect to the polypeptide domains from which they are formed.

With this tailor-made generation of therapeutics by combining two polypeptide domains, different modes of action can be combined, such as dual targeting (combination of two binding entities, bispecific or multispecific binder), targeting and payload delivery (combination of binding entity (targeting) and effector entity (payload), such as antibody-conjugates), or combined receptor inhibition (combination of two receptors and/or ligands). The resulting therapeutics are single therapeutic molecules simultaneously performing the modes of action of the individual polypeptide domains. Therewith, e.g., additive/synergistic effect is expected in comparison to single domain therapeutic molecules.

By using already available therapeutic entities, such as those e.g. derived from therapeutic antibodies, a fast and easy production of multi-domain therapeutic molecule can be achieved.

For example, avidity engineered binding molecules/antibodies can bind to two or more cell surface markers present on a single cell. This binding is only avid if all/both binding entities simultaneously bind to the cell. For this purpose low to medium, low to high, or medium to high affine antibodies are especially suited. This allows also on the other hand to exclude less specific combinations of binding specificities during a screening process.

With such an approach the generation of tailor-made and, thus, highly efficacious therapeutic molecules is possible. These molecules will have fewer or less severe/reduced side effects because of their improved properties, such as targeted delivery (e.g. payload for tumor cells) and improved targeting to target cells based on higher selectivity and specificity of the targeting component (comprising at least two binding molecules).

The higher selectivity and specificity of a multispecific binder is effected by the simultaneous binding (avidity) of the combination of two "low affinity" binders, which reduces or prevents altogether potential "off-target" binding.

Methods as Reported Herein

One aspect as reported herein is a method for producing a polypeptide comprising at least two polypeptide domains comprising the step of cultivating a cell comprising
  a) a nucleic acid encoding a soluble sortase A with a C-terminal endoplasmic reticulum retention signal,
  b) a nucleic acid encoding a first polypeptide domain comprising at its C-terminus or in its C-terminal region a sortase motif followed by an endoplasmic reticulum retention signal, and
  c) a nucleic acid encoding a second polypeptide domain comprising at its N-terminus at least a diglycine motif, whereby the cell secretes the sortase A(-ligated) conjugate of the first polypeptide domain and the second polypeptide domain, thereby producing a polypeptide comprising at least two polypeptide domains.

One aspect as reported herein is a method for producing a multispecific binder comprising at least two binding entities comprising the step of
cultivating a cell comprising
  a) a nucleic acid encoding a soluble sortase A with a C-terminal endoplasmic reticulum retention signal,
  b) a nucleic acid encoding a first binding entity comprising at its C-terminus or in its C-terminal region a sortase motif followed by an endoplasmic reticulum retention signal, and
  c) a nucleic acid encoding a second binding entity comprising at its N-terminus at least a diglycine motif,
whereby the cell secretes the sortase A(-ligated) conjugate of the first binding entity and the second binding entity,
whereby the first binding entity specifically binds to a first antigen or target and the second binding entity specifically binds to a second antigen or target,
thereby producing a multispecific binder comprising at least two binding entities.

One aspect as reported herein is a method for selecting a multispecific binder that specifically binds to two different epitopes or antigens comprising the step of
selecting from a multitude of multispecific binders comprising different combinations of a first binding entity and a second binding entity a multispecific binder that specifically binds to two different epitopes or antigens.

One aspect as reported herein is a method for selecting a bispecific antibody comprising the following steps
  (i) determining the cell surface makers present in a cell-containing sample and selecting thereof at least a first surface marker and a second surface marker,
  (ii) transfecting a cell with (a) a nucleic acid encoding an antibody Fab fragment, or an antibody scFab, or a scFv antibody comprising within the 20 C-terminal amino acid residues the amino acid sequence LPXTG (SEQ ID NO: 01, wherein X can be any amino acid residue) followed by an endoplasmic reticulum retention signal KDEL (SEQ ID NO: 02), whereby the Fab fragment, or the scFab fragment, or the scFv antibody specifically binds to the first surface marker or its ligand, (b) a nucleic acid encoding a one-armed antibody fragment comprising a full length antibody heavy chain, a full length antibody light chain, and an antibody heavy chain Fc-region polypeptide, whereby the full length antibody heavy chain and the full length antibody light chain are cognate antibody chains complementary to each other and the pair of variable domains (VH and VL) thereof forms an antigen binding site that specifically binds to the second surface marker or its ligand, whereby the full length antibody heavy chain and the antibody heavy chain Fc-region polypeptide are covalently linked to each other via one or more disulfide bonds forming an antibody hinge region, and whereby the antibody heavy chain Fc-region polypeptide has an oligoglycine $G_m$ (m=2, or 3, or 4, or 5) (SEQ ID NO: 53) amino acid sequence at its N-terminus, and (c) a nucleic acid encoding a soluble sortase A with a C-terminal endoplasmic reticulum retention signal,
and thereby producing the bispecific antibody.

One aspect as reported herein is a method for determining a combination of antigen binding sites comprising the following steps
  (i) determining the binding specificity and/or selectivity and/or affinity and/or effector function and/or in vivo half-life of a multitude of bispecific antibodies prepared by combining (a) each member of a first multitude of antibody Fab fragments, or antibody scFab fragments, or scFv antibody fragments whereby each member comprises within the 20 C-terminal amino acid residues the amino acid sequence LPXTG (SEQ ID NO: 01, wherein X can be any amino acid residue) followed by an endoplasmic reticulum retention signal KDEL (SEQ ID NO: 02), whereby the Fab fragment, or the scFab fragment, or the scFv antibody specifically binds to a first epitope or antigen, with (b) each member of a multitude of one-armed antibody fragments comprising a full length antibody heavy chain, a full length antibody light chain, and an antibody heavy chain Fc-region polypeptide, whereby the full length antibody heavy chain and the full length antibody light chain are cognate antibody chains complementary to each other and the pair of variable domains (VH and VL) thereof forms an antigen binding site that specifically binds to a second epitope or antigen, whereby the full length antibody heavy chain and the antibody heavy chain Fc-region polypeptide are covalently linked to each other via one or more disulfide bonds forming an antibody hinge region, and whereby the antibody heavy chain Fc-region polypeptide has an oligoglycine $G_m$ (m=2, or 3, or 4, or 5) (SEQ ID NO: 53) amino acid sequence at its N-terminus, using a sortase A-mediated enzymatic coupling reaction,
and
  (ii) choosing the bispecific antibody with suitable binding specificity and/or selectivity and/or affinity and/or effector function and/or in vivo half-life and thereby determining a combination of antigen binding sites.

In the following embodiments of all methods as reported herein are given.

In one embodiment of all aspects is the sortase A the sortase A of *Staphylococcus aureus* (*S. aureus*). In one embodiment the nucleic acid encoding a (soluble) sortase A with a C-terminal endoplasmic reticulum retention signal encodes an amino acid sequence of SEQ ID NO: 51 or SEQ ID NO: 52.

In one embodiment the members of the multitude of multispecific binders are each obtained by a method as reported herein.

In one embodiment a multispecific binder is selected based on its binding specificity and/or selectivity and/or affinity and/or effector function and/or in vivo half-life.

In one embodiment the binding entity is a cognate pair of an antibody heavy chain variable domain and an antibody light chain variable domain.

In one embodiment the multispecific binder is a bispecific antibody comprising two or four binding entities.

In one embodiment the first polypeptide domain and the second polypeptide domain are selected independently of each other from full length antibody, scFv, scFab, antibody heavy chain, antibody light chain, antibody heavy chain Fc-region fragment, pair of antibody light chain variable domain and antibody heavy chain variable domain, antigen binding antibody fragments, VH, VL, CH1, CH2, CH3, CH4, CL, antibody hinge region, cytokine, receptor, receptor ligand, detectable label, tag, and partner of a binding pair.

In one embodiment the endoplasmic reticulum retention signal is selected from SEQ ID NO: 02 (KDEL), SEQ ID NO: 03 (HDEL), or SEQ ID NO: 04 (SFIXXXXMP).

In one embodiment the sortase motif is LPXTG (SEQ ID NO: 01, wherein X can be any amino acid residue).

In one embodiment the first binding domain or the first binding entity comprises or has within the 20 C-terminal amino acid residues the amino acid sequence LPXTG (SEQ ID NO: 01, wherein X can be any amino acid residue).

In one embodiment the cell is a mammalian cell or a yeast cell. In one embodiment the mammalian cell is selected from a HEK cell, a CHO cell, or a BHK cell.

In one embodiment the Fc-region comprises a mutation of the naturally occurring amino acid residue at position 329 and at least one further mutation of at least one amino acid residue selected from the group comprising amino acid residues at position 228, 233, 234, 235, 236, 237, 297, 318, 320, 322 and 331 to a different residue, wherein the residues in the Fc-region are numbered according to the EU index of Kabat. The change of these specific amino acid residues results in an altering of the effector function of the Fc-region compared to the non-modified (wild-type) Fc-region.

In one embodiment the binding entity is selected from (or the first binding entity and the second binding entity are selected independently of each other from) the group of a darpin domain based binding entity, an anticalin domain based binding entity, a T-cell receptor fragment like scTCR domain based binding entity, a camel VH domain based binding entity, a tenth fibronectin 3 domain based binding entity, a tenascin domain based binding entity, a cadherin domain based binding entity, an ICAM domain based binding entity, a titin domain based binding entity, a GCSF-R domain based binding entity, a cytokine receptor domain based binding entity, a glycosidase inhibitor domain based binding entity, a superoxide dismutase domain based binding entity, or antibody fragments like Fab, or scFab, or scFv fragment.

In one embodiment the first polypeptide domain comprises i) the amino acid sequence LPXTG (SEQ ID NO: 01, wherein X can be any amino acid residue) in its C-terminal amino acid sequence region (i.e. within the twenty C-terminal amino acid residues) and ii) the endoplasmic reticulum retention signal KDEL (SEQ ID NO: 02) at its C-terminus, and the second polypeptide domain comprises an oligoglycine $G_m$ (m=2, or 3, or 4, or 5) (SEQ ID NO: 53) at its N-terminus.

In one embodiment the second polypeptide domain or the second binding entity comprises an oligoglycine $G_m$ (m=2, or 3, or 4, or 5) amino acid sequence at its N-terminus.

In one embodiment the human antibody Fc-region is of human IgG1 subclass, or of human IgG2 subclass, or of human IgG3 subclass, or of human IgG4 subclass.

In one embodiment the antibody Fc-region is a human antibody Fc-region of the human IgG1 subclass, or of the human IgG4 subclass.

In one embodiment the human antibody Fc-region comprises a mutation of the naturally occurring amino acid residue at least at one of the following amino acid positions 228, 233, 234, 235, 236, 237, 297, 318, 320, 322, 329, and/or 331 to a different residue, wherein the residues in the antibody Fc-region are numbered according to the EU index of Kabat.

In one embodiment the human antibody Fc-region comprises a mutation of the naturally occurring amino acid residue at position 329 and at least one further mutation of at least one amino acid residue selected from the group comprising amino acid residues at position 228, 233, 234, 235, 236, 237, 297, 318, 320, 322 and 331 to a different residue, wherein the residues in the Fc-region are numbered according to the EU index of Kabat. The change of these specific amino acid residues results in an altering of the effector function of the Fc-region compared to the non-modified (wild-type) Fc-region.

In one embodiment the human antibody Fc-region has a reduced affinity to the human FcγRIIIA, and/or FcγRIIA, and/or FcγRI compared to a conjugate comprising the corresponding wild-type IgG Fc-region.

In one embodiment the amino acid residue at position 329 in the human antibody Fc-region is substituted with glycine, or arginine, or an amino acid residue large enough to destroy the proline sandwich within the Fc-region.

In one embodiment the mutation in the human antibody Fc-region of the naturally occurring amino acid residue is at least one of S228P, E233P, L234A, L235A, L235E, N297A, N297D, P329G, and/or P331S.

In one embodiment the mutation is L234A and L235A if the antibody Fc-region is of human IgG1 subclass, or S228P and L235E if the antibody Fc-region is of human IgG4 subclass.

In one embodiment the antibody Fc-region comprises the mutation P329G.

In one embodiment the antibody Fc-region comprises the mutation T366W in the first heavy chain Fc-region polypeptide and the mutations T366S, L368A and Y407V in the second heavy chain Fc-region polypeptide, wherein the numbering is according to the EU index of Kabat.

In one embodiment the antibody Fc-region comprises the mutation S354C in the first heavy chain Fc-region polypeptide and the mutation Y349C in the second heavy chain Fc-region polypeptide.

In one embodiment the antibody Fc-region comprises besides a mutation of the amino acid residue proline at position 329 at least one further addition, mutation, or deletion of an amino acid residue in the Fc-region that is correlated with increased stability of the antibody Fc-region conjugate.

In one embodiment the further addition, mutation, or deletion of an amino acid residue in the Fc-region is at position 228 and/or 235 of the Fc-region if the Fc-region is of IgG4 subclass. In one embodiment the amino acid residue serine at position 228 and/or the amino acid residue leucine at position 235 is/are substituted by another amino acid. In one embodiment the antibody Fc-region conjugate comprises a proline residue at position 228 (mutation of the serine residue to a proline residue). In one embodiment the antibody Fc-region conjugate comprises a glutamic acid residue at position 235 (mutation of the leucine residue to a glutamic acid residue).

In one embodiment the Fc-region comprises three amino acid mutations. In one embodiment the three amino acid mutations are P329G, S228P and L235E mutation (P329G SPLE).

In one embodiment the further addition, mutation, or deletion of an amino acid residue in the Fc-region is at position 234 and/or 235 of the Fc-region if the Fc-region is of IgG1 subclass. In one embodiment the amino acid residue leucine at position 234 and/or the amino acid residue leucine at position 235 is/are mutated to another amino acid.

In one embodiment the Fc-region comprises an amino acid mutation at position 234, wherein the leucine amino acid residue is mutated to an alanine amino acid residue.

In one embodiment the Fc-region comprises an amino acid mutation at position 235, wherein the leucine amino acid residue is mutated to an alanine amino acid residue.

In one embodiment the Fc-region comprises an amino acid mutation at position 329, wherein the proline amino acid residue is mutated to a glycine amino acid residue, an amino acid mutation at position 234, wherein the leucine amino acid residue is mutated to an alanine amino acid residue, and an amino acid mutation at position 235, wherein the leucine amino acid residue is mutated to an alanine amino acid residue.

Fc-region variants with increased affinity for FcRn have longer serum half-lives, and such molecules will have useful applications in methods of treating mammals where long systemic half-life of the administered antibody or Fc-region conjugate is desired, e.g., to treat a chronic disease or disorder.

Antibody Fc-region conjugates with decreased FcRn binding affinity have shorter serum half-lives, and such molecules will have useful applications in methods of treating mammals where a shorter systemic half-life of the administered antibody Fc-region conjugate is desired, e.g. to avoid toxic side effects or for in vivo diagnostic imaging applications. Fc-region fusion polypeptides or conjugates with decreased FcRn binding affinity are less likely to cross the placenta, and thus may be utilized in the treatment of diseases or disorders in pregnant women.

An Fc-region with altered binding affinity for FcRn is in one embodiment an Fc-region with an amino acid alteration at one or more of the amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447.

The Fc-region is in one embodiment an Fc-region with one or more amino acid alterations at the amino acid positions 252, 253, 254, 255, 288, 309, 386, 388, 400, 415, 433, 435, 436, 439, and/or 447.

An Fc-region which display increased binding to FcRn comprises in one embodiment one or more amino acid alterations at the amino acid positions 238, 256, 265, 272, 286, 303, 305, 307, 311, 312, 317, 340, 356, 360, 362, 376, 378, 380, 382, 413, 424, and/or 434.

In one embodiment the Fc-region is an Fc-region of the IgG1 subclass and comprises the amino acid mutations P329G, and/or L234A and L235A.

In one embodiment the Fc-region is an Fc-region of the IgG4 subclass and comprises the amino acid mutations P329G, and/or S228P and L235E.

In one embodiment the antibody Fc-region comprises the mutation T366W in the first heavy chain Fc-region polypeptide and the mutations T366S, L368A and Y407V in the second heavy chain Fc-region polypeptide, wherein the numbering is according to the EU index of Kabat.

In one embodiment the antibody Fc-region comprises the mutation S354C in the first heavy chain Fc-region polypeptide and the mutation Y349C in the second heavy chain Fc-region polypeptide.

Enzymatic Conjugation Using Sortase A

A multi-domain polypeptide can be obtained in vivo by using the enzyme sortase A.

Many gram-positive bacteria use sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a LPXTG (SEQ ID NO: 01) amino acid sequence motif and cleaves the amide bond between the Thr and Gly by means of an active-site Cys. This peptide cleaving reaction results in a sortase A-substrate thioester intermediate. In a second step the thioester acyl-enzyme intermediate is resolved by nucleophilic attack of an amino group of an oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This new technique enables the introduction of natural and synthetic functionalities into LPXTG-tagged (SEQ ID NO: 1) recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (Tsukiji, S. and Nagamune, T., ChemBioChem 10 (2009) 787-798; Popp, M. W.-L. and Ploegh, H. L., Angew. Chem. Int. Ed. 50 (2011) 5024-5032).

It has been shown that a triglycine and even a diglycine motif of the amino component is sufficient for the SrtA-mediated ligation step (Clancy, K. W., et al., Peptide Science 94 (2010) 385-396).

For the enzymatic conjugation a soluble truncated sortase A lacking the membrane-spanning region (SrtA; amino acid residues 60-206 of *Staphylococcus aureus* SrtA) can be used (Ton-That, H., et al., Proc. Natl. Acad. Sci. USA 96 (1999) 12424-12429; Ilangovan, H., et al., Proc. Natl. Acad. Sci. USA 98 (2001) 6056-6061).

Any polypeptide domain comprising an oligoglycine motif at least at one of its N-termini ($G_m$, m=2, or 3, or 4, or 5) (SEQ ID NO: 53) can be expressed und purified from the supernatant of eukaryotic cells (e.g. HEK293 cells, CHO cells).

A binding entity (e.g. a single chain antigen binding polypeptide such as a scFv, a scFab, or a darpin, or a multi chain antigen binding polypeptide such as a dsFv or a Fab) comprising the SrtA recognition motif at the C-terminus of one polypeptide chain can be expressed und purified from the supernatant of eukaryotic cells (e.g. HEK293 cells, CHO cells).

The "Combimatrix" Approach

It is desirable to combine a first binding entity, such as an antibody Fab fragment, with another specific binding entity, such as a second antibody Fab fragment or a one-armed antibody fragment comprising a full length heavy chain and its cognate full length light chain and a disulfide linked heavy chain Fc-region polypeptide. In addition it is possible to screen, whether a first binding entity shows better properties when linking it to a number of different other binding entities. Using a so-called Combimatrix approach, a multitude of combinations of binding entities can be addressed in an easy way. It has to be pointed out that the second binding entities can either bind to different targets/epitopes/antigens, or can bind to the same antigen but to different epitopes, or can bind to the same epitope but be different variants of a single binding entity (e.g. humanization candidates).

In this scenario, an automated platform process can be performed. Any platform that uses e.g. 96-well plates or other high throughput formats is suitable, such as an Eppendorf epMotion 5075vac pipetting robot.

First, cloning of the binding entity encoding constructs is performed. The plasmids with the binding entity encoding nucleic acids are usually obtained by gene synthesis or PCR amplification, whereby the C-terminal region of one encoded binding entity contains a sortase-motif, and an endoplasmic reticulum retention signal, and the N-terminal region of the respective other binding entity comprises an N-terminal oligoglycine motif comprising/of at least two consecutive glycine residues (diglycine). The plasmids are individually transferred into a separate well of a multi-well plate (a whole plate can be loaded). Thereafter, the plasmids are digested with a restriction enzyme mix that cuts out the binding entity-coding region. It is desirable to design all gene syntheses and/or PCR primers in a way that only one restriction enzyme mix is needed for all plasmids. Afterwards, an optional cleaning step yields purified DNA fragments. These fragments are ligated into a plasmid backbone that had been cut out of an acceptor vector with the same restriction mix as mentioned above. Alternatively, the cloning procedure can be performed by a SLIC-mediated cloning step. After ligation, the automated platforms transfers all ligation mixes into a further multi-well plate with competent E. coli cells (e.g. Top10 Multi Shot, Invitrogen), and a transformation reaction is performed. The cells are cultivated to the desired density. From an aliquot of the cultivation mixture glycerol stocks can be obtained. From the culture plasmid is isolated (e.g. using a plasmid isolation mini kit (e.g. NucleoSpin 96 Plasmid, Macherey& Nagel)). Plasmid identity is verified by digesting an aliquot with an appropriate restriction mix and SDS-gel electrophoresis (e.g. E-Gel 48, Invitrogen). Afterwards a new plate can be loaded with an aliquot of the plasmid for performing a control sequencing reaction.

In the next step the binding entities are expressed. To this end, HEK cells are seeded onto a multi-well plate (e.g. a 48-well-plate) and are transfected with the respective isolated plasmid combinations (containing the binding entity-coding regions in appropriate backbone vectors) together with a plasmid encoding soluble sortase bearing a C-terminal endoplasmic retention signal. Thus, HEK cells are co-transfected with three expression plasmids: i) a plasmid encoding a binding entity that has a C-terminal His-tag, sortase motif and endoplasmic retention signal (in N-terminal to C-terminal direction), ii) a plasmid encoding a binding entity that has an N-terminal oligo glycine motif of at least two glycine residues and iii) a plasmid encoding soluble sortase that has a C-terminal endoplasmic retention signal. Transfected HEK cells are cultivated for several days and subsequently culture supernatants are harvested (e.g. by filtrating through a 1.2 μm and a 0.22 μm filter plate by using a vacuum station). Titers can be monitored by performing e.g. an ELISA.

The binding entities are linked to the each other using a sortase-mediated transpeptidation reaction during the expression in vivo. This is achieved as the binding domain comprising the C-terminal sortase recognition motif comprises an endoplasmic reticulum retention signal. The soluble sortase employed comprises the same endoplasmic reticulum retention signal at its C-terminus. Thus, both molecules are almost completely retained in the endoplasmic reticulum. Upon entry of the second polypeptide domain into the endoplasmic reticulum the enzymatic conjugation reaction takes place and the enzymatic conjugate, which is devoid of the endoplasmic reticulum retention signal, which is removed during the enzymatic transpeptidation reaction, is secreted into the cultivation medium. The conjugates can be harvested from the cultivation medium by using a His-tag selection procedure (the culture supernatant is applied onto e.g. His MultiTrap HP plates (GE Healthcare) and filtrated, whereby all molecules that comprise a His-tag are bound to the matrix (i.e. the conjugates) and can be eluted after washing with an appropriate elution buffer, while all other molecules will not bind to the chromatography material.

The multispecific binding molecules can be made using the Combimatrix approach, see the following Table below).

|   | 1  | 2  | 3  | 4  | 5  | 6  | 7  | 8  | 9  | 10  | 11  |
|---|----|----|----|----|----|----|----|----|----|-----|-----|
| A | 1A | 2A | 3A | 4A | 5A | 6A | 7A | 8A | 9A | 10A | 11A |
| B | 1B | ...| ...| ...| ...| ...| ...| ...| ...| ... | ... |
| C | 1C | ...| ...| ...| ...| ...| ...| ...| ...| ... | ... |
| D | 1D | ...| ...| ...| ...| ...| ...| ...| ...| ... | ... |
| E | 1E | ...| ...| ...| ...| ...| ...| ...| ...| ... | ... |
| F | 1F | ...| ...| ...| ...| ...| ...| ...| ...| ... | ... |
| G | 1G | ...| ...| ...| ...| ...| ...| ...| ...| ... | 11G |

The wells of the first column of a multi-well plate denote different plasmids encoding first binding entities comprising a C-terminal sortase motif (designated in arabic numbers, e.g. 1 to 11 for a 96-well plate). The wells of the first row of the same plate denote different plasmids encoding second binding entities comprising an oligoglycine at the N-terminus/in the N-terminal region (excluding the first row, designated in letters, e.g. A to G). Thereafter all plasmids encoding a first binding entity of the first row are combined with all plasmids encoding a second binding entity of the first column (e.g. resulting in 77 combinations in a 96-well plate), designated by a combination of number and letter (e.g. 1A to 11G). In addition, plasmid encoding sortase is added to all wells. All combinations are co-transfected into HEK cells and thereby expressed and conjugated in vivo by the sortase A comprising an endoplasmic reticulum retention signal. After the enzymatic in vivo conjugation has been performed, an optional purification step can be performed. The multispecific binding molecules are then ready for evaluation in biochemical or cell-based assays.

III. Recombinant Methods

Suitable host cells for cloning and/or expression/secretion of polypeptide-encoding vectors include prokaryotic and eukaryotic cells described herein. For example, polypeptides may be produced in bacteria, in particular when glycosylation and Fc effector function are not needed (see, e.g., U.S. Pat. Nos. 5,648,237, 5,789,199, and 5,840,523, Charlton, Methods in Molecular Biology 248 (2003) 245-254 (B.K.C. Lo, (ed.), Humana Press, Totowa, N.J.), describing expression of antibody fragments in E. coli.). After expression, the polypeptide may be isolated from the bacterial cell paste in a soluble fraction or may be isolated from the insoluble fraction, so-called inclusion bodies which can be solubilized and the polypeptide be refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension culture may be useful. Other examples of useful mammalian host cell lines are the COS-7 cell line (monkey kidney CV1 cell transformed by SV40; the HEK293 cell line (human embryonic kidney) BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line, as described, e.g., in Mather, et al., Annals N.Y. Acad. Sci. 383 (1982) 44-68; the MRCS cell line; and FS4 cell-s line. Other useful mammalian host cell lines include the CHO cell line (Chinese hamster ovary cell), including DHFR negative CHO cell lines (Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B.K.C. Lo, (ed.), Humana Press, Totowa, N.J.).

IV. Methods and Compositions for Diagnostics and Detection

In certain embodiments, any of the bispecific antibodies provided herein is useful for detecting the presence of one or both antigens in a biological sample. The term "detecting" as used herein encompasses quantitative or qualitative detection. In certain embodiments, a biological sample comprises a cell or tissue, such as biopsies of cancer cells.

In one embodiment, a bispecific antibody for use in a method of diagnosis or detection is provided. In a further aspect, a method of detecting the presence of cancer cells in a biological sample is provided. In certain embodiments, the method comprises contacting the biological sample with a bispecific antibody as described herein under conditions permissive for binding of the bispecific antibody to its antigen or antigens, and detecting whether a complex is formed between the bispecific antibody and its antigen or antigens. Such method may be an in vitro or in vivo method.

Exemplary disorders that may be diagnosed using an antibody of the invention include cancer.

In certain embodiments, labeled bispecific antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

V. Pharmaceutical Formulations

Pharmaceutical formulations of a bispecific antibody as described herein are prepared by mixing such antibody having the desired degree of purity with one or more optional pharmaceutically acceptable carriers (Remington's Pharmaceutical Sciences, 16th edition, Osol, A. (ed.), (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly (vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

VI. Therapeutic Methods and Compositions

Any of the bispecific antibodies provided herein may be used in therapeutic methods.

In one aspect, a bispecific antibody for use as a medicament is provided. In further aspects, a bispecific antibody for use in treating cancer is provided. In certain embodiments, a bispecific antibody for use in a method of treatment is provided. In certain embodiments, the invention provides a bispecific antibody for use in a method of treating an individual having cancer comprising administering to the individual an effective amount of the bispecific antibody. In one such embodiment, the method further comprises administering to the individual an effective amount of at least one additional therapeutic agent, e.g., as described below. In further embodiments, the invention provides a bispecific antibody for use in removing/killing/lysing cancer cells. In certain embodiments, the invention provides a bispecific antibody for use in a method for removing/killing/lysing cancer cells in an individual comprising administering to the individual an effective of the bispecific antibody to remove/kill/lyse cancer cells. An "individual" according to any of the above embodiments can be a human.

In a further aspect, the invention provides for the use of a bispecific antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. In a further embodiment, the medicament is for removing/killing/lysing cancer cells. In a further embodiment, the medicament is for use in a method of removing/killing/lysing cancer cells in an individual comprising administering to the individual an amount effective of the medicament to remove/kill/lyse cancer cells. An "individual" according to any of the above embodiments may be a human.

In a further aspect, the invention provides a method for treating cancer. In one embodiment, the method comprises administering to an individual having cancer an effective amount of a bispecific antibody. In one such embodiment, the method further comprises administering to the individual an effective amount of at least one additional therapeutic agent, as described below. An "individual" according to any of the above embodiments may be a human.

In a further aspect, the invention provides a method for removing/killing/lysing cancer cells in an individual. In one embodiment, the method comprises administering to the individual an effective amount of the bispecific antibody to remove/kill/lyse cancer cells. In one embodiment, an "individual" is a human.

In a further aspect, the invention provides pharmaceutical formulations comprising any of the bispecific antibodies provided herein, e.g., for use in any of the above therapeutic methods. In one embodiment, a pharmaceutical formulation comprises any of the bispecific antibodies provided herein and a pharmaceutically acceptable carrier. In another embodiment, a pharmaceutical formulation comprises any of the bispecific antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a cytotoxic agent or a chemotherapeutic agent.

Such combination therapies noted above encompass combined administration (where two or more therapeutic agents are included in the same or separate formulations), and separate administration, in which case, administration of the antibody of the invention can occur prior to, simultaneously with, and/or following, the administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, intradermal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various points in time, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally, formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a bispecific antibody.

VII. Articles of Manufacture

In another aspect of the invention, an article of manufacture containing materials useful for the treatment, prevention and/or diagnosis of the disorders described above is provided. The article of manufacture comprises a container and a label or package insert on, or associated with, the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a bispecific antibody.

EXAMPLES

The following examples are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention.

Materials and Methods
Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany)

Protein Determination

The protein concentration of purified polypeptides was determined by determining the optical density (OD) at 280 nm, using the molar extinction coefficient calculated on the basis of the amino acid sequence of the polypeptide.

Example 1

Generation of Expression Plasmids for Antibodies and Antibody Fragments Including Single Chain Fab Antibody Fragments Desired proteins were expressed by transient transfection of human embryonic kidney cells (HEK 293). For the expression of a desired gene/protein (e.g. full length antibody heavy chain, full length antibody light chain, scFab fragments or an Fc-chain containing an oligoglycine at its N-terminus) a transcription unit comprising the following functional elements was used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence (SS),
- a gene/protein to be expressed, and
- the bovine growth hormone polyadenylation sequence (BGH pA).

In addition to the expression unit/cassette including the desired gene to be expressed the basic/standard mammalian expression plasmid contains
- an origin of replication from the vector pUC18 which allows replication of this plasmid in E. coli, and
- a beta-lactamase gene which confers ampicillin resistance in E. coli.

a) Generation of an Expression Plasmid for a Single Chain Fab Fragment (scFab) with C-Terminal his-Tag, Sortase Motif, and ER Retention Signal The scFab encoding fusion gene comprising a C-terminal His-tag, followed by a sortase recognition motif and an endoplasmic retention (ER) signal was assembled by fusing a DNA fragment coding for the respective sequence elements (His6-tag (HHHHHH, SEQ ID NO: 07), sortase motif (LPETGGS, SEQ ID NO: 28), and ER retention signal (KDEL, SEQ ID NO: 02), separated each by a short GS sequence element (GSHHHHHHGSLPETGGSKDEL (SEQ ID NO: 29) to a rat-human chimeric single chain Fab molecule (Vkappa-huCkappa-linker-Vheavy-huCH1).

The expression plasmid for the transient expression of a scFab fragment with a C-terminal His-tag, sortase motif and ER retention signal fusion protein in HEK293 cells comprised besides the scFab fragment with C-terminal His-tag, sortase motif and ER retention signal expression cassette, an origin of replication from the vector pUC18, which allows replication of this plasmid in *E. coli*, and a beta-lactamase gene which confers ampicillin resistance in *E. coli*. The transcription unit of the scFab fragment with C-terminal His-tag, sortase motif and ER retention signal fusion gene comprises the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a scFab (Vkappa-huCkappa-linker-Vheavy-huCH1) encoding nucleic acid,
- a His-tag encoding nucleic acid,
- a sortase recognition motif encoding nucleic acid,
- an ER retention signal encoding nucleic acid, and
- the bovine growth hormone polyadenylation sequence (BGH pA).

The amino acid sequence of the mature scFab fragment of anti-transferrin receptor antibody 3D8 with C-terminal His-tag, sortase motif, and ER retention signal fusion protein is (SEQ ID NO: 30)
DIQMTQSPASLSASLEEIVTITCQASQDIGNWLAWYQQKPGKSPQLLIYG

ATSLADGVPSRFSGSRSGTQFSLKISRVQVEDIGIYYCLQAYNTPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECGGGGSGGGGSGGGGSGGGGSGGGGSGGGGSGGEVQL

VESGGGLVQPGNSLTLSCVASGFTFSNYGMHWIRQAPKKGLEWIAMIYYD

SSKMNYADTVKGRFTISRDNSKNTLYLEMNSLRSEDTAMYYCAVPTSHYV

VDVWGQGVSVTVSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSCGSHHHHHHGSLPETGGSKDEL.

b) Generation of the Expression Plasmid for a Single Chain Fab Fragment (scFab) with N-Terminal Glycine-Serine Motif The scFab fusion gene comprising an N-terminal glycine-serine motif was assembled by fusing a DNA fragment coding for the respective sequence element ((G4S)2, SEQ ID NO: 31) to a rat-human chimeric single chain Fab molecule (Vkappa-huCkappa-linker-Vheavy-huCH1).

The expression plasmid for the transient expression of a scFab fragment with an N-terminal glycine-serine motif in HEK293 cells comprised besides the scFab fragment with an N-terminal glycine-serine motif expression cassette an origin of replication from the vector pUC18, which allows replication of this plasmid in *E. coli*, and a beta-lactamase gene which confers ampicillin resistance in *E. coli*. The transcription unit of the scFab fragment with an N-terminal glycine-serine motif fusion gene comprises the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a (G4S)2 motif (SEQ ID NO: 31) encoding nucleic acid,
- a scFab (Vkappa-huCkappa-linker-Vheavy-huCH1) encoding nucleic acid, and
- the bovine growth hormone polyadenylation sequence (BGH pA).

The amino acid sequence of the mature scFab fragment of anti-transferrin receptor antibody 3D8 with N-terminal glycine-serine motif is (SEQ ID NO: 32)
GGGGSGGGGSDIQMTQSPASLSASLEEIVTITCQASQDIGNWLAWYQQKP

GKSPQLLIYGATSLADGVPSRFSGSRSGTQFSLKISRVQVEDIGIYYCLQ

AYNTPWTFGGGTKVEIKRTVAAPSVFIFPPSDEQLKSGTASVVCLLNNFY

PREAKVQWKVDNALQSGNSQESVTEQDSKDSTYSLSSTLTLSKADYEKHK

VYACEVTHQGLSSPVTKSFNRGECGGGGSGGGGSGGGGSGGGGSGGGGSG

GGGSGGEVQLVESGGGLVQPGNSLTLSCVASGFTFSNYGMHWIRQAPKKG

LEWIAMIYYDSSKMNYADTVKGRFTISRDNSKNTLYLEMNSLRSEDTAMY

YCAVPTSHYVVDVWGQGVSVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC.

c) Generation of the Expression Plasmid for an Antibody Fc-Region Fragment (FC) with N-Terminal Triple Glycine Motif The FC fusion gene comprising an N-terminal triple glycine motif was assembled by fusing a DNA fragment coding for the respective sequence element (GGG, SEQ ID NO: 33) to a human antibody heavy chain Fc-region molecule.

The expression plasmid for the transient expression of an antibody Fc-region fragment with N-terminal triple glycine motif in HEK293 cells comprised besides the antibody heavy chain Fc-region with N-terminal triple glycine motif expression cassette an origin of replication from the vector pUC18, which allows replication of this plasmid in *E. coli*, and a beta-lactamase gene which confers ampicillin resistance in *E. coli*. The transcription unit of the antibody Fc-region fragment (FC) with N-terminal triple glycine motif fusion gene comprises the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a GGG (SEQ ID NO: 33) encoding nucleic acid,
- an Fc-region encoding nucleic acid, and
- the bovine growth hormone polyadenylation sequence (BGH pA).

The amino acid sequence of the mature antibody Fc-region fragment with N-terminal triple glycine motif is (SEQ ID NO: 34)
GGGDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

d) Expression Plasmid for an Antibody Heavy and Light Chains

Expression plasmids coding for the following polypeptides/proteins were constructed according to the methods as outlined before:

Pertuzumab heavy chain variable domain combined with a human heavy chain constant region of the subclass IgG1 containing a T366W mutation:

(SEQ ID NO: 35)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK.

Pertuzumab light chain variable domain combined with a human kappa light chain constant region:

(SEQ ID NO: 36)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

Trastuzumab heavy chain variable domain combined with a human heavy chain constant region of the subclass IgG1 containing a T366S, L368A, and Y407V mutation:

(SEQ ID NO: 37)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VCTLPPSRDELTKNQVSLSCAVKGFYPSDIAVEWESNGQPENNYKTTPPV

LDSDGSFFLVSKLTVDKSRWQQGNVFSCSVMHEALHNHYTQKSLSLSPG

K.

Trastuzumab light chain variable domain combined with a human kappa light chain constant region:

(SEQ ID NO: 38)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

antibody VH-CH1 fragment comprising a Pertuzumab heavy chain variable domain and a human heavy chain constant region 1 (CH1) of the subclass IgG1 containing a C-terminal GGGSHHHHHHGSLPETGGSKDEL (SEQ ID NO: 55) amino acid sequence:

(SEQ ID NO: 39)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCGGGSHHHHHHGSLPETGGSKDEL.

antibody VH-CH1 fragment comprising a Pertuzumab heavy chain variable domain and a human heavy chain constant region 1 (CH1) of the subclass IgG1 containing a C-terminal GSHHHHHHGSLPETGGSKDEL (SEQ ID NO: 29) sequence:

(SEQ ID NO: 40)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCGSHHHHHHGSLPETGGSKDEL.

antibody VH-CH1 fragment comprising a Pertuzumab heavy chain variable domain and a human heavy chain constant region 1 (CH1) of the subclass IgG1 containing a C-terminal HHHHHHGSLPETGGSKDEL (SEQ ID NO: 56) sequence:

(SEQ ID NO: 41)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCHHHHHHGSLPETGGSKDEL.

antibody VH-CH1 fragment comprising a Trastuzumab heavy chain variable domain and a human heavy chain constant region 1 (CH1) of the subclass IgG1 containing a C-terminal GGGSHHHHHHGSLPETGGSGSKDEL (SEQ ID NO: 57) sequence:

(SEQ ID NO: 42)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCGGGSHHHHHHGSLPETGGSGSKDEL.

antibody VH-CH1 fragment comprising a Trastuzumab heavy chain variable domain and a human heavy chain constant region 1 (CH1) of the subclass IgG1 containing a C-terminal GSHHHHHHGSLPETGGSGSKDEL (SEQ ID NO: 58) sequence:

(SEQ ID NO: 43)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCGSHHHHHHGSLPETGGSGSKDEL.

antibody VH-CH1 fragment comprising a Trastuzumab heavy chain variable domain and a human heavy chain constant region 1 (CH1) of the subclass IgG1 containing a C-terminal HHHHHHGSLPETGGSGSKDEL (SEQ ID NO: 59) sequence:

(SEQ ID NO: 44)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCHHHHHHGSLPETGGSGSKDEL.

heavy chain Fc-region polypeptide (human IgG1(CH2-CH3)) with T366S, L368A, and Y407V mutation containing an N-terminal GGGDKTHTCPPC (SEQ ID NO: 60) sequence:

(SEQ ID NO: 45)
GGGDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVCTLPPSRDELTKNQVSLSC

AVKGFYPSDIAVEWESNGQPENNYKTTPPVLDSDGSFFLVSKLTVDKSRW

QQGNVFSCSVMHEALHNHYTQKSLSLSPGK.

heavy chain Fc-region polypeptide (human IgG1(CH2-CH3)) with T366S, L368A, and Y407V mutation containing an N-terminal GGHTCPPC (SEQ ID NO: 61) sequence:

(SEQ ID NO: 46)
GGHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVCTLPPSRDELTKNQVSLSCAVKG

FYPSDIAVEWESNGQPENNYKTTPPVLDSDGSFFLYSKLTVDKSRWQQGN

VFSCSVMHEALHNHYTQKSLSLSPGK.

heavy chain Fc-region polypeptide (human IgG1(CH2-CH3)) with T366S, L368A, and Y407V mutation containing an N-terminal GGCPPC (SEQ ID NO: 62) sequence:

(SEQ ID NO: 47)
GGCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVCTLPPSRDELTKNQVSLSCAVKGFY

PSDIAVEWESNGQPENNYKTTPPVLDSDGSFFLVSKLTVDKSRWQQGNVF

SCSVMHEALHNHYTQKSLSLSPGK.

heavy chain Fc-region polypeptide (human IgG1(CH2-CH3)) with T366W mutation containing an N-terminal GGGDKTHTCPPC (SEQ ID NO: 60) sequence:

(SEQ ID NO: 48)
GGGDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPCRDELTKNQVSLWC

LVKGFYPSDIAVEWESNGQPENNYKTTPPVLDSDGSFFLYSKLTVDKSRW

QQGNVFSCSVMHEALHNHYTQKSLSLSPGK.

heavy chain Fc-region polypeptide (human IgG1(CH2-CH3)) with T366W mutations containing an N-terminal GGHTCPPC (SEQ ID NO: 61) sequence:

(SEQ ID NO: 49)
GGHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPCRDELTKNQVSLWCLVKG

FYPSDIAVEWESNGQPENNYKTTPPVLDSDGSFFLYSKLTVDKSRWQQGN

VFSCSVMHEALHNHYTQKSLSLSPGK.

heavy chain Fc-region polypeptide (human IgG1(CH2-CH3)) with T366W mutation containing an N-terminal GGCPPC (SEQ ID NO: 62) sequence:

(SEQ ID NO: 50)
GGCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPCRDELTKNQVSLWCLVKGFY

PSDIAVEWESNGQPENNYKTTPPVLDSDGSFFLYSKLTVDKSRWQQGNVF

SCSVMHEALHNHYTQKSLSLSPGK.

Example 2

Generation of an Expression Plasmid for Soluble *S. aureus* Sortase A with C-Terminal ER Retention Signal The sortase fusion gene comprising a C-terminal ER retention signal was assembled by fusing a DNA fragment coding for an ER retention signal (KDEL) (SEQ ID NO: 2) to an N-terminally truncated *Staphylococcus aureus* sortase A (60-206) molecule (SrtA-KDEL) ("KDEL" disclosed as SEQ ID NO: 2).

The expression plasmid for the transient expression of soluble sortase with ER retention signal in HEK293 cells comprised besides the soluble sortase with ER retention signal expression cassette an origin of replication from the vector pUC18, which allows replication of this plasmid in *E. coli*, and a beta-lactamase gene which confers ampicillin resistance in *E. coli*. The transcription unit of the soluble sortase with ER retention signal comprises the following functional elements:

the immediate early enhancer and promoter from the human cytomegalovirus (P-CMV) including intron A, a human heavy chain immunoglobulin 5'-untranslated region (5'UTR), a murine immunoglobulin heavy chain signal sequence, an N-terminally truncated *S. aureus* sortase A encoding nucleic acid, an ER retention signal encoding nucleic acid, and the bovine growth hormone polyadenylation sequence (BGH pA).

As the C-terminal amino acid residue of the N-terminally truncated *S. aureus* sortase A is already a lysine (K) only the amino acid sequence DEL had to be fused at the C-terminus of the enzyme in order to establish a functional ER retention signal (KDEL) (SEQ ID NO: 2).

The amino acid sequence of the mature soluble sortase with ER retention signal (KDEL) (SEQ ID NO: 2) is

```
                                           (SEQ ID NO: 51)
QAKPQIPKDKSKVAGYIEIPDADIKEPVYPGPATPEQLNRGVSFAEENES

LDDQNISIAGHTFIDRPNYQFTNLKAAKKGSMVYFKVGNETRKYKMTSIR

DVKPTDVGVLDEQKGKDKQLTLITCDDYNEKTGVWEKRKIFVATEVKDE

L.
```

The amino acid sequence of the mature soluble sortase with GSKDEL (SEQ ID NO: 63) endoplasmic reticulum retention signal is

```
                                           (SEQ ID NO: 52)
QAKPQIPKDKSKVAGYIEIPDADIKEPVYPGPATPEQLNRGVSFAEENES

LDDQNISIAGHTFIDRPNYQFTNLKAAKKGSMVYFKVGNETRKYKMTSIR

DVKPTDVGVLDEQKGKDKQLTLITCDDYNEKTGVWEKRKIFVATEVKGSK

DEL.
```

Example 3

Transient Expression, Purification and Analytical Characterization of the Conjugates Generated in Vivo by Sortase-Mediated Transpeptidation The conjugates were generated in vivo in transiently transfected HEK293 cells (human embryonic kidney cell line 293-derived) cultivated in F17 Medium (Invitrogen Corp.). For transfection "293-Free" Transfection Reagent (Novagen) was used. The N- and C-terminally extended scFab molecules as described above as well as the soluble sortase each were expressed from individual expression plasmids. Transfections were performed as specified in the manufacturer's instructions. Fusion protein-containing cell culture supernatants were harvested three to seven (3-7) days after transfection. Supernatants were stored at reduced temperature (e.g. −80° C.) until purification.

General information regarding the recombinant expression of human immunoglobulins in e.g. HEK293 cells is given in: Meissner, P. et al., Biotechnol. Bioeng. 75 (2001) 197-203.

The culture supernatants were filtered and subsequently purified by $Ni^{2+}$-ion affinity chromatography. The secreted proteins comprising a His-tag were captured by affinity chromatography using Ni Sepharose™ high performance His-Trap HP (GE Healthcare). Unbound proteins were removed by washing with 10 mM Tris buffer pH 7.5 containing 500 mM NaCl and 30 mM imidazole. The bound His-tag containing proteins were eluted with 10 mM Tris buffer pH 7.5 containing 500 mM NaCl and 500 mM imidazole. Size exclusion chromatography on Superdex 200™ (GE Healthcare) was used as second purification step. The size exclusion chromatography was performed in 20 mM histidine buffer, 0.14 M NaCl, pH 6.0. The recovered proteins were dialyzed into 10 mM histidine buffer pH 6.0 containing 140 mM NaCl, and stored at −80° C.

The protein concentration of the proteins was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue. Aggregate content of the Fc-fusion protein preparations was determined by high-performance SEC using a SK3000SWx1 analytical size-exclusion column (Tosohaas, Stuttgart, Germany). The integrity of the amino acid backbone of reduced Fc fusion proteins were verified by Nano Electrospray QTOF mass spectrometry after removal of N-glycans by enzymatic treatment with peptide-N-glycosidase F (Roche Applied Science).

What is claimed:

1. A method for producing a polypeptide comprising at least two polypeptide domains comprising the step of cultivating a cell comprising
   a) a nucleic acid encoding a soluble S. aureus sortase A with a C-terminal endoplasmic reticulum retention signal,
   b) a nucleic acid encoding a first polypeptide domain comprising at its C-terminus a sortase motif followed by an endoplasmic reticulum retention signal, wherein the sortase motif comprises LPXTG (SEQ ID NO: 01, wherein X can be any amino acid residue) and
   c) a nucleic acid encoding a second polypeptide domain comprising an oligoglycine $G_m$ (m=2, or 3, or 4, or 5) (SEQ ID NO: 53) at its N-terminus,
   wherein the cell secretes a sortase A conjugate of the first polypeptide domain and the second polypeptide domain,
   thereby producing a polypeptide comprising at least two polypeptide domains.

2. A method for producing a multispecific binder comprising at least two binding entities comprising the step of cultivating a cell comprising
   a) a nucleic acid encoding a soluble S. aureus sortase A with a C-terminal endoplasmic reticulum retention signal,
   b) a nucleic acid encoding a first binding entity comprising at its C-terminus a sortase motif followed by an endoplasmic reticulum retention signal, wherein the sortase motif comprises LPXTG (SEQ ID NO: 01, wherein X can be any amino acid residue) and
   c) a nucleic acid encoding a second binding entity comprising an oligoglycine $G_m$ (m=2, or 3, or 4, or 5) (SEQ ID NO: 53) at its N-terminus,
   wherein the cell secretes a sortase A conjugate of the first binding entity and the second binding entity, and wherein the first binding entity specifically binds to a first antigen or target and the second binding entity specifically binds to a second antigen or target,
   thereby producing a multispecific binder comprising at least two binding entities.

3. A method for selecting a multispecific binder that specifically binds to two different epitopes or antigens comprising the step of
   selecting from a multitude of multispecific binders comprising different combinations of a first binding entity and a second binding entity a multispecific binder that specifically binds to two different epitopes or antigens,
   wherein the members of the multitude of multispecific binders are each obtained by a method according to claim 2.

4. The method according to claim 3, wherein the multispecific binder is selected based on its binding specificity and/or selectivity and/or affinity and/or effector function and/or in vivo half-life.

5. The method according to claim 2, wherein the first and second binding entities comprise a cognate pair of an antibody heavy chain variable domain and an antibody light chain variable domain.

6. The method according to claim 2, wherein the multispecific binder is a bispecific antibody comprising two or four binding entities.

7. The method according to claim 1, wherein the first polypeptide domain and the second polypeptide domain are selected independently of each other from the group consisting of a full length antibody, a scFv, a scFab, an antibody heavy chain, an antibody light chain, an antibody heavy chain Fc-region fragment, a pair of antibody light chain variable domain and antibody heavy chain variable domain, a VH, a VL, a CH1, a CH2, a CH3, a CH4, a CL, an antibody hinge region, a cytokine, a receptor, a receptor ligand, a detectable label, a tag, and a partner of a binding pair.

8. The method according to claim 1 or 2, wherein the endoplasmic reticulum retention signal is selected from the group consisting of SEQ ID NO: 02 (KDEL), SEQ ID NO: 03 (HDEL), and SEQ ID NO: 04 (SFIXXXXMP).

9. The method according to claim 1 or 2, wherein the first polypeptide domain or the first binding entity has within the 20 C-terminal amino acid residues the amino acid sequence LPXTG (SEQ ID NO: 01, wherein X can be any amino acid residue).

10. The method according to claim 1 or 2, wherein the cell is a mammalian cell or a yeast cell.

11. The method according to claim 10, wherein the mammalian cell is selected from the group consisting of a HEK cell, a CHO cell, and a BHK cell.

12. A method for producing a bispecific antibody comprising the following steps
  (i) determining the cell surface makers present in a cell containing sample and selecting thereof at least a first surface marker and a second surface marker,
  (ii) transfecting a cell with
    (a) a nucleic acid encoding an antibody Fab fragment, or an antibody scFab, or a scFv antibody comprising within the 20 C-terminal amino acid residues the amino acid sequence LPXTG (SEQ ID NO: 01, wherein X can be any amino acid residue) followed by an endoplasmic reticulum retention signal KDEL (SEQ ID NO: 02), wherein the Fab fragment or scFv antibody specifically binds to the first surface marker or its ligand,
    (b) a nucleic acid encoding an one-armed antibody fragment comprising a full length antibody heavy chain, a full length antibody light chain, and an antibody heavy chain Fc-region polypeptide, wherein the full length antibody heavy chain and the full length antibody light chain are cognate antibody chains complementary to each other and the pair of variable domains (VH and VL) thereof forms an antigen binding site that specifically binds to the second surface marker or its ligand, and wherein the full length antibody heavy chain and the antibody heavy chain Fc-region polypeptide are covalently linked to each other via one or more disulfide bonds forming an antibody hinge region, and wherein the antibody heavy chain Fc-region polypeptide has an oligoglycine $G_m$ (m=2, or 3, or 4, or 5) (SEQ ID NO: 53) amino acid sequence at its N-terminus, and
    (c) a nucleic acid encoding a soluble *S. aureus* sortase A with a C-terminal endoplasmic reticulum retention signal,
  and thereby producing the bispecific antibody.

13. The method according to claim 6 or 12, wherein the Fc-region comprises a mutation of the naturally occurring amino acid residue at position 329 and at least one further mutation of at least one amino acid residue selected from the group consisting of amino acid residues at position 228, 233, 234, 235, 236, 237, 297, 318, 320, 322 and 331 to a different residue, wherein the residues in the Fc-region are numbered according to the EU index of Kabat.

* * * * *

SEQUENCE LISTING

```
<160> NUMBER OF SEQ ID NOS: 64

<210> SEQ ID NO 1
<211> LENGTH: 5
<212> TYPE: PRT
<213> ORGANISM: Staphylococcus aureus
<220> FEATURE:
<221> NAME/KEY: MOD_RES
<222> LOCATION: (3)..(3)
<223> OTHER INFORMATION: Any amino acid

<400> SEQUENCE: 1

Leu Pro Xaa Thr Gly
1               5

<210> SEQ ID NO 2
<211> LENGTH: 4
<212> TYPE: PRT
<213> ORGANISM: Homo sapiens
```

```
<400> SEQUENCE: 2

Lys Asp Glu Leu
1

<210> SEQ ID NO 3
<211> LENGTH: 4
<212> TYPE: PRT
<213> ORGANISM: Saccharomyces cerevisiae

<400> SEQUENCE: 3

His Asp Glu Leu
1

<210> SEQ ID NO 4
<211> LENGTH: 9
<212> TYPE: PRT
<213> ORGANISM: Adenovirus type 2
<220> FEATURE:
<221> NAME/KEY: MOD_RES
<222> LOCATION: (4)..(7)
<223> OTHER INFORMATION: Any amino acid

<400> SEQUENCE: 4

Ser Phe Ile Xaa Xaa Xaa Xaa Met Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Arg Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 19
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 8

Lys Asp His Leu Ile His Asn Val His Lys Glu Phe His Ala His Ala
1               5                   10                  15

His Asn Lys

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Tyr Lys Asp Asp Asp Asp Lys
1               5

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Trp Arg His Pro Gln Phe Gly Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ser His Pro Gln Phe Glu Lys
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 13

Met Asp Val Glu Ala Trp Leu Gly Ala Arg
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Asp Val Glu Ala Trp Leu Gly Ala Arg Val Pro Leu Val Glu Thr
1               5                   10                  15

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Gln Lys Leu Ile Ser Glu Glu Asp Leu
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Glu Thr Ala Ala Ala Lys Phe Glu Arg Gln His Met Asp Ser
1               5                   10                  15

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Arg Arg Trp Lys Lys Asn Phe Ile Ala Val Ser Ala Ala Asn Arg
```

```
                1               5                   10                  15
Phe Lys Lys Ile Ser Ser Ser Gly Ala Leu
                20                      25

<210> SEQ ID NO 19
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
                20                  25                  30

Gly Thr Thr Cys Gln Val Leu Asn Pro Tyr Tyr Ser Gln Cys Leu
            35                  40                  45

<210> SEQ ID NO 20
<211> LENGTH: 32
<212> TYPE: PRT
<213> ORGANISM: Butyrivibrio fibrisolvens

<400> SEQUENCE: 20

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
                20                  25                  30

<210> SEQ ID NO 21
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chitin-binding-domain

<400> SEQUENCE: 21

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
                20                  25                  30

His Thr Ser Leu Ala Gly Trp Glu Pro Ser Asn Val Pro Ala Leu Trp
            35                  40                  45

Gln Leu Gln
        50

<210> SEQ ID NO 22
<211> LENGTH: 209
<212> TYPE: PRT
<213> ORGANISM: Chondrus crispus

<400> SEQUENCE: 22

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
                20                  25                  30

Arg Val Val Phe Asp His Trp Lys Glu Ala Lys Pro Lys Thr Pro Tyr
```

```
            35                  40                  45
Ala Ala Leu Pro Met Leu Thr Val Asp Gly Met Gln Val Ala Gln Ser
 50                  55                  60

Asp Ala Ile Leu Arg Tyr Cys Gly Lys Leu Ala Gly Leu Tyr Pro Ser
 65                  70                  75                  80

Asp Pro Leu Glu Ala Lys Val Asp Glu Val Gly Gly Val Ile Asp
                 85                  90                  95

Asp Val Thr His Ala Met Tyr Arg Tyr Arg Gly Asp Asp Lys Asp Lys
                100                 105                 110

Leu Arg Glu Glu Arg Asp Lys Phe Ser Lys Val Asp Val Pro Arg Tyr
                115                 120                 125

Val Gly Ala Leu Glu Lys Arg Leu Glu Ala Phe Gly Asp Gly Pro Trp
                130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
                180                 185                 190

His Pro Lys Val Thr Glu Trp Tyr Glu Lys Lys Pro Val Lys Met Phe
                195                 200                 205

Ser

<210> SEQ ID NO 23
<211> LENGTH: 396
<212> TYPE: PRT
<213> ORGANISM: Escherichia coli

<400> SEQUENCE: 23

Met Lys Ile Lys Thr Gly Ala Arg Ile Leu Ala Leu Ser Ala Leu Thr
 1                   5                  10                  15

Thr Met Met Phe Ser Ala Ser Ala Leu Ala Lys Ile Glu Glu Gly Lys
                 20                  25                  30

Leu Val Ile Trp Ile Asn Gly Asp Lys Gly Tyr Asn Gly Leu Ala Glu
                 35                  40                  45

Val Gly Lys Lys Phe Glu Lys Asp Thr Gly Ile Lys Val Thr Val Glu
 50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
                115                 120                 125

Leu Ile Ala Tyr Pro Ile Ala Val Glu Ala Leu Ser Leu Ile Tyr Asn
                130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
```

```
                195                 200                 205
Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
370                 375                 380

Glu Ala Leu Lys Asp Ala Gln Thr Arg Ile Thr Lys
385                 390                 395

<210> SEQ ID NO 24
<211> LENGTH: 222
<212> TYPE: PRT
<213> ORGANISM: Homo sapiens

<400> SEQUENCE: 24

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175
```

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 25
<211> LENGTH: 222
<212> TYPE: PRT
<213> ORGANISM: Homo sapiens

<400> SEQUENCE: 25

Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

<210> SEQ ID NO 26
<211> LENGTH: 107
<212> TYPE: PRT
<213> ORGANISM: Homo sapiens

<400> SEQUENCE: 26

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

```
Glu Ser Thr Tyr Arg Trp Ser Val Leu Thr Val Leu His Gln Asp Trp
 65                  70                  75                  80

Leu Asn Gly Lys Glu Tyr Lys Cys Lys Val Ser Asn Lys Ala Leu Pro
                 85                  90                  95

Ala Pro Ile Glu Lys Thr Ile Ser Lys Ala Lys
            100                 105

<210> SEQ ID NO 27
<211> LENGTH: 106
<212> TYPE: PRT
<213> ORGANISM: Homo sapiens

<400> SEQUENCE: 27

Gly Gln Pro Arg Glu Pro Gln Val Tyr Thr Leu Pro Pro Ser Arg Asp
  1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase motif with C-terminal GS linker

<400> SEQUENCE: 28

Leu Pro Glu Thr Gly Gly Ser
  1               5

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Hexa-histidine - sortase motif- endoplasmic
      reticulum  retention signal - tag

<400> SEQUENCE: 29

Gly Ser His His His His His His Gly Ser Leu Pro Glu Thr Gly Gly
  1               5                  10                  15

Ser Lys Asp Glu Leu
            20

<210> SEQ ID NO 30
<211> LENGTH: 488
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Mature scFab fragment of anti-transferrin
      receptor antibody 3D8 with C-terminal His-tag, sortase motif, and
      ER retention signal fusion protein

<400> SEQUENCE: 30

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Ser
210                 215                 220

Gly Gly Gly Gly Ser Gly Gly Gly Ser Gly Gly Gly Ser Gly
225                 230                 235                 240

Gly Gly Ser Gly Gly Glu Val Gln Leu Val Glu Ser Gly Gly
                245                 250                 255

Leu Val Gln Pro Gly Asn Ser Leu Thr Leu Ser Cys Val Ala Ser Gly
            260                 265                 270

Phe Thr Phe Ser Asn Tyr Gly Met His Trp Ile Arg Gln Ala Pro Lys
        275                 280                 285

Lys Gly Leu Glu Trp Ile Ala Met Ile Tyr Tyr Asp Ser Ser Lys Met
290                 295                 300

Asn Tyr Ala Asp Thr Val Lys Gly Arg Phe Thr Ile Ser Arg Asp Asn
305                 310                 315                 320

Ser Lys Asn Thr Leu Tyr Leu Glu Met Asn Ser Leu Arg Ser Glu Asp
                325                 330                 335

Thr Ala Met Tyr Tyr Cys Ala Val Pro Thr Ser His Tyr Val Val Asp
            340                 345                 350

Val Trp Gly Gln Gly Val Ser Val Thr Val Ser Ser Ala Ser Thr Lys
        355                 360                 365
```

```
Gly Pro Ser Val Phe Pro Leu Ala Pro Ser Ser Lys Ser Thr Ser Gly
    370                 375                 380
Gly Thr Ala Ala Leu Gly Cys Leu Val Lys Asp Tyr Phe Pro Glu Pro
385                 390                 395                 400
Val Thr Val Ser Trp Asn Ser Gly Ala Leu Thr Ser Gly Val His Thr
                405                 410                 415
Phe Pro Ala Val Leu Gln Ser Ser Gly Leu Tyr Ser Leu Ser Ser Val
            420                 425                 430
Val Thr Val Pro Ser Ser Leu Gly Thr Gln Thr Tyr Ile Cys Asn
        435                 440                 445
Val Asn His Lys Pro Ser Asn Thr Lys Val Asp Lys Lys Val Glu Pro
    450                 455                 460
Lys Ser Cys Gly Ser His His His His His His Gly Ser Leu Pro Glu
465                 470                 475                 480
Thr Gly Gly Ser Lys Asp Glu Leu
                485

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Gly Ser Gly Gly Gly Gly Ser
1               5                   10

<210> SEQ ID NO 32
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mature scFab fragment of anti-transferrin
      receptor antibody 3D8 with N-terminal glycine-serine motif

<400> SEQUENCE: 32

Gly Gly Gly Gly Ser Gly Gly Gly Ser Asp Ile Gln Met Thr Gln
1               5                   10                  15
Ser Pro Ala Ser Leu Ser Ala Ser Leu Glu Glu Ile Val Thr Ile Thr
                20                  25                  30
Cys Gln Ala Ser Gln Asp Ile Gly Asn Trp Leu Ala Trp Tyr Gln Gln
            35                  40                  45
Lys Pro Gly Lys Ser Pro Gln Leu Leu Ile Tyr Gly Ala Thr Ser Leu
    50                  55                  60
Ala Asp Gly Val Pro Ser Arg Phe Ser Gly Ser Arg Ser Gly Thr Gln
65                  70                  75                  80
Phe Ser Leu Lys Ile Ser Arg Val Gln Val Glu Asp Ile Gly Ile Tyr
                85                  90                  95
Tyr Cys Leu Gln Ala Tyr Asn Thr Pro Trp Thr Phe Gly Gly Gly Thr
            100                 105                 110
Lys Val Glu Ile Lys Arg Thr Val Ala Ala Pro Ser Val Phe Ile Phe
        115                 120                 125
Pro Pro Ser Asp Glu Gln Leu Lys Ser Gly Thr Ala Ser Val Val Cys
    130                 135                 140
```

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
            165                 170                 175

Asp Ser Lys Asp Ser Thr Tyr Ser Leu Ser Ser Thr Leu Thr Leu Ser
        180                 185                 190

Lys Ala Asp Tyr Glu Lys His Lys Val Tyr Ala Cys Glu Val Thr His
    195                 200                 205

Gln Gly Leu Ser Ser Pro Val Thr Lys Ser Phe Asn Arg Gly Glu Cys
210                 215                 220

Gly Gly Gly Gly Ser Gly Gly Gly Ser Gly Gly Gly Gly Ser Gly
225                 230                 235                 240

Gly Gly Gly Ser Gly Gly Gly Ser Gly Gly Gly Ser Gly Gly
                245                 250                 255

Glu Val Gln Leu Val Glu Ser Gly Gly Gly Leu Val Gln Pro Gly Asn
            260                 265                 270

Ser Leu Thr Leu Ser Cys Val Ala Ser Gly Phe Thr Phe Ser Asn Tyr
        275                 280                 285

Gly Met His Trp Ile Arg Gln Ala Pro Lys Lys Gly Leu Glu Trp Ile
290                 295                 300

Ala Met Ile Tyr Tyr Asp Ser Ser Lys Met Asn Tyr Ala Asp Thr Val
305                 310                 315                 320

Lys Gly Arg Phe Thr Ile Ser Arg Asp Asn Ser Lys Asn Thr Leu Tyr
            325                 330                 335

Leu Glu Met Asn Ser Leu Arg Ser Glu Asp Thr Ala Met Tyr Tyr Cys
        340                 345                 350

Ala Val Pro Thr Ser His Tyr Val Val Asp Val Trp Gly Gln Gly Val
    355                 360                 365

Ser Val Thr Val Ser Ser Ala Ser Thr Lys Gly Pro Ser Val Phe Pro
370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
            405                 410                 415

Ser Gly Ala Leu Thr Ser Gly Val His Thr Phe Pro Ala Val Leu Gln
        420                 425                 430

Ser Ser Gly Leu Tyr Ser Leu Ser Ser Val Val Thr Val Pro Ser Ser
    435                 440                 445

Ser Leu Gly Thr Gln Thr Tyr Ile Cys Asn Val Asn His Lys Pro Ser
450                 455                 460

Asn Thr Lys Val Asp Lys Lys Val Glu Pro Lys Ser Cys
465                 470                 475

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly
1

<210> SEQ ID NO 34

<211> LENGTH: 230
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mature antibody Fc-region fragment with N-terminal triple glycine motif

<400> SEQUENCE: 34

```
Gly Gly Gly Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230
```

<210> SEQ ID NO 35
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Pertuzumab heavy chain variable domain combined with a human heavy chain constant region of the subclass IgG1 containing a T366W mutation

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
```

```
                35                  40                  45
Ala Asp Val Asn Pro Asn Ser Gly Gly Ser Ile Tyr Asn Gln Arg Phe
 50                      55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Cys Arg Asp Glu Leu Thr Lys Asn Gln Val Ser Leu Trp
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445

Lys
```

```
<210> SEQ ID NO 36
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Pertuzumab light chain variable domain combined
      with a human kappa light chain constant region

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Trastuzumab heavy chain variable domain
      combined with a human heavy chain constant region of the subclass
      IgG1 containing a T366S, L368A, and Y407V mutation

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

```
<210> SEQ ID NO 38
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Trastuzumab light chain variable domain
      combined with a human kappa light chain constant region

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody VH-CH1 fragment comprising a
      Pertuzumab heavy chain variable domain and a human heavy chain
      constant region 1 (CH1) of the subclass IgG1 containing a
      C-terminal GGGSHHHHHHGSLPETGGSKDEL amino acid sequence

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
```

```
                35                  40                  45
Ala Asp Val Asn Pro Asn Ser Gly Gly Ser Ile Tyr Asn Gln Arg Phe
 50                  55                  60
Lys Gly Arg Phe Thr Leu Ser Val Asp Arg Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asn Leu Gly Pro Ser Phe Tyr Phe Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Gly Gly
                210                 215                 220
Gly Ser His His His His His His Gly Ser Leu Pro Glu Thr Gly Gly
225                 230                 235                 240
Ser Lys Asp Glu Leu
                245

<210> SEQ ID NO 40
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody VH-CH1 fragment comprising a
      Pertuzumab heavy chain variable domain and a human heavy chain
      constant region 1 (CH1) of the subclass IgG1 containing a
      C-terminal GSHHHHHHGSLPETGGSKDEL sequence

<400> SEQUENCE: 40

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Thr Asp Tyr
                 20                  25                  30
Thr Met Asp Trp Val Arg Gln Ala Pro Gly Lys Gly Leu Glu Trp Val
                 35                  40                  45
Ala Asp Val Asn Pro Asn Ser Gly Gly Ser Ile Tyr Asn Gln Arg Phe
 50                  55                  60
Lys Gly Arg Phe Thr Leu Ser Val Asp Arg Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asn Leu Gly Pro Ser Phe Tyr Phe Asp Tyr Trp Gly Gln Gly
                100                 105                 110
Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
    210                 215                 220

His His His His His His Gly Ser Leu Pro Glu Thr Gly Gly Ser Lys
225                 230                 235                 240

Asp Glu Leu

<210> SEQ ID NO 41
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody VH-CH1 fragment comprising a
      Pertuzumab heavy chain variable domain and a human heavy chain
      constant region 1 (CH1) of the subclass IgG1 containing a
      C-terminal HHHHHHGSLPETGGSKDEL sequence

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Lys Val Glu Pro Lys Ser Cys His His
    210                 215                 220

His His His His Gly Ser Leu Pro Glu Thr Gly Gly Ser Lys Asp Glu
225                 230                 235                 240

Leu

<210> SEQ ID NO 42
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody VH-CH1 fragment comprising a
      Trastuzumab heavy chain variable domain and a human heavy chain
      constant region 1 (CH1) of the subclass IgG1 containing a
      C-terminal GGGSHHHHHHGSLPETGGSGSKDEL sequence

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Ser His His His His His His Gly Ser Leu Pro Glu Thr Gly
225                 230                 235                 240

Gly Ser Gly Ser Lys Asp Glu Leu
                245

<210> SEQ ID NO 43
<211> LENGTH: 246
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: Antibody VH-CH1 fragment comprising a
      Trastuzumab heavy chain variable domain and a human heavy chain
      constant region 1 (CH1) of the subclass IgG1 containing a
      C-terminal GSHHHHHHGSLPETGGSGSKDEL sequence

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Ser His His His His His His Gly Ser Leu Pro Glu Thr Gly Gly Ser
225                 230                 235                 240

Gly Ser Lys Asp Glu Leu
            245

<210> SEQ ID NO 44
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody VH-CH1 fragment comprising a
      Trastuzumab heavy chain variable domain and a human heavy chain
      constant region 1 (CH1) of the subclass IgG1 containing a
      C-terminal HHHHHHGSLPETGGSGSKDEL sequence

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys His
210                 215                 220

His His His His Gly Ser Leu Pro Glu Thr Gly Gly Ser Gly Ser
225                 230                 235                 240

Lys Asp Glu Leu

<210> SEQ ID NO 45
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain Fc-region polypeptide (human
      IgG1(CH2-CH3)) with T366S, L368A and Y407V mutation containing a
      N-terminal gggdkthtcppc sequence

<400> SEQUENCE: 45

Gly Gly Gly Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu

```
            115                 120                 125
Pro Gln Val Cys Thr Leu Pro Pro Ser Arg Asp Glu Leu Thr Lys Asn
        130                 135                 140

Gln Val Ser Leu Ser Cys Ala Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Val Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
210                 215                 220

Ser Leu Ser Pro Gly Lys
225                 230

<210> SEQ ID NO 46
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain Fc-region polypeptide (human
      IgG1(CH2-CH3)) with T366S, L368A and Y407V mutation containing a
      N-terminal gghtcppc sequence

<400> SEQUENCE: 46

Gly Gly His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Cys
        115                 120                 125

Thr Leu Pro Pro Ser Arg Asp Glu Leu Thr Lys Asn Gln Val Ser Leu
    130                 135                 140

Ser Cys Ala Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Val Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220
```

-continued

Gly Lys
225

<210> SEQ ID NO 47
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain Fc-region polypeptide (human
      IgG1(CH2-CH3)) with T366S, L368A and Y407V mutation containing a
      N-terminal ggcppc sequence

<400> SEQUENCE: 47

Gly Gly Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 48
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain Fc-region polypeptide (human
      IgG1(CH2-CH3)) with T366W mutation containing a N-terminal
      gggdkthtcppc sequence

<400> SEQUENCE: 48

Gly Gly Gly Asp Lys Thr His Thr Cys Pro Pro Cys Pro Ala Pro Glu
1               5                   10                  15

```
Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
 50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Cys Arg Asp Glu Leu Thr Lys Asn
130                 135                 140

Gln Val Ser Leu Trp Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 49
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain Fc-region polypeptide (human
      IgG1(CH2-CH3)) with T366W mutations containing a N-terminal
      gghtcppc sequence

<400> SEQUENCE: 49

Gly Gly His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
```

```
              115                 120                 125
Thr Leu Pro Pro Cys Arg Asp Glu Leu Thr Lys Asn Gln Val Ser Leu
    130                 135                 140

Trp Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 50
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain Fc-region polypeptide (human
      IgG1(CH2-CH3)) with T366W mutation containing a N-terminal
      ggcppc sequence

<400> SEQUENCE: 50

Gly Gly Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

<210> SEQ ID NO 51
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mature soluble sortase with ER retention signal

<400> SEQUENCE: 51

```
Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
    130                 135                 140

Glu Val Lys Asp Glu Leu
145                 150
```

<210> SEQ ID NO 52
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mature soluble sortase with GSKDEL ER retention
      signal

<400> SEQUENCE: 52

```
Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110
```

```
Gln Lys Gly Lys Asp Lys Gln Leu Thr Leu Ile Thr Cys Asp Asp Tyr
            115                 120                 125

Asn Glu Lys Thr Gly Val Trp Glu Lys Arg Lys Ile Phe Val Ala Thr
        130                 135                 140

Glu Val Lys Gly Ser Lys Asp Glu Leu
145                 150

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: May or may not be present

<400> SEQUENCE: 53

Gly Gly Gly Gly Gly
1               5

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser His His His His His His Gly Ala Pro Pro Pro Ser Leu Pro
1               5                   10                  15

Glu Thr Gly Gly Ser Lys Asp Glu Leu
            20                  25

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Ser His His His His His Gly Ser Leu Pro Glu Thr
1               5                   10                  15

Gly Gly Ser Lys Asp Glu Leu
            20

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His His His His His His Gly Ser Leu Pro Glu Thr Gly Gly Ser Lys
1               5                   10                  15

Asp Glu Leu

<210> SEQ ID NO 57
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Ser His His His His His Gly Ser Leu Pro Glu Thr
1               5                   10                  15

Gly Gly Ser Gly Ser Lys Asp Glu Leu
            20                  25

<210> SEQ ID NO 58
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser His His His His His His Gly Ser Leu Pro Glu Thr Gly Gly
1               5                   10                  15

Ser Gly Ser Lys Asp Glu Leu
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His His His His His His Gly Ser Leu Pro Glu Thr Gly Gly Ser Gly
1               5                   10                  15

Ser Lys Asp Glu Leu
            20

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Gly Asp Lys Thr His Thr Cys Pro Pro Cys
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly His Thr Cys Pro Pro Cys
1               5

<210> SEQ ID NO 62
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Cys Pro Pro Cys
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Ser Lys Asp Glu Leu
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His His His His His
1               5
```